(12) United States Patent
Graham

(10) Patent No.: US 10,624,530 B2
(45) Date of Patent: Apr. 21, 2020

(54) FLEXIBLE STRUCTURES

(71) Applicant: Howard Graham, Temecula, CA (US)

(72) Inventor: Howard Graham, Temecula, CA (US)

(73) Assignee: Howard Graham, Temecula, CA (US)

( * ) Notice: Subject to any disclaimer, the term of this patent is extended or adjusted under 35 U.S.C. 154(b) by 211 days.

(21) Appl. No.: 15/028,401

(22) PCT Filed: Oct. 31, 2014

(86) PCT No.: PCT/US2014/063546
§ 371 (c)(1),
(2) Date: Apr. 8, 2016

(87) PCT Pub. No.: WO2015/066536
PCT Pub. Date: May 7, 2015

(65) Prior Publication Data
US 2016/0235274 A1 Aug. 18, 2016

Related U.S. Application Data

(60) Provisional application No. 61/898,281, filed on Oct. 31, 2013.

(51) Int. Cl.
| | |
|---|---|
| *A61B 1/005* | (2006.01) |
| *A01K 85/00* | (2006.01) |
| *A61B 1/00* | (2006.01) |
| *A61B 17/00* | (2006.01) |
| *A61M 25/00* | (2006.01) |
| *A61M 25/01* | (2006.01) |

(52) U.S. Cl.
CPC ............ *A61B 1/005* (2013.01); *A01K 85/00* (2013.01); *A01K 85/005* (2013.01); *A61B 1/0011* (2013.01); *A61B 1/0055* (2013.01); *A61B 17/00234* (2013.01); *A61M 25/005* (2013.01); *A61B 2017/00314* (2013.01); *A61B 2017/00327* (2013.01); *A61M 25/0012* (2013.01); *A61M 25/0105* (2013.01); *A61M 25/0138* (2013.01)

(58) Field of Classification Search
CPC ........... A61B 1/005; A61B 1/008; A61B 1/01; A61B 1/0055; A61B 1/00–32; B25J 18/06; B25J 18/005; F16F 1/328; F16F 1/32; F16F 1/322; F16F 1/324; F16F 1/326
USPC ........................................ 600/141; 43/18.1 R
See application file for complete search history.

(56) References Cited

U.S. PATENT DOCUMENTS

| | | | | |
|---|---|---|---|---|
| 3,060,972 | A * | 10/1962 | Sheldon | A61B 1/0055 138/120 |
| 6,068,250 | A * | 5/2000 | Hawkins | F16F 1/328 267/148 |
| 6,669,184 | B2 * | 12/2003 | Cai | F16F 1/328 267/162 |
| 2005/0131279 | A1 * | 6/2005 | Boulais | A61B 1/00059 600/141 |
| 2010/0160735 | A1 * | 6/2010 | Bakos | A61B 17/3417 600/141 |
| 2012/0071720 | A1 * | 3/2012 | Banik | A61B 1/00059 600/118 |

(Continued)

*Primary Examiner* — Lee E Sanderson
*Assistant Examiner* — Michael C Romanowski
(74) *Attorney, Agent, or Firm* — K&L Gates LLP; Louis C. Cullman; Brian J. Novak

(57) ABSTRACT

Flexible frameworks are described including a plurality of at least one structural component having a waveform axially stacked and configured to form at least one internal conduit.

13 Claims, 16 Drawing Sheets

(56) References Cited

U.S. PATENT DOCUMENTS

2013/0312564 A1* 11/2013 Kim ................... B25J 18/06
74/490.04

* cited by examiner

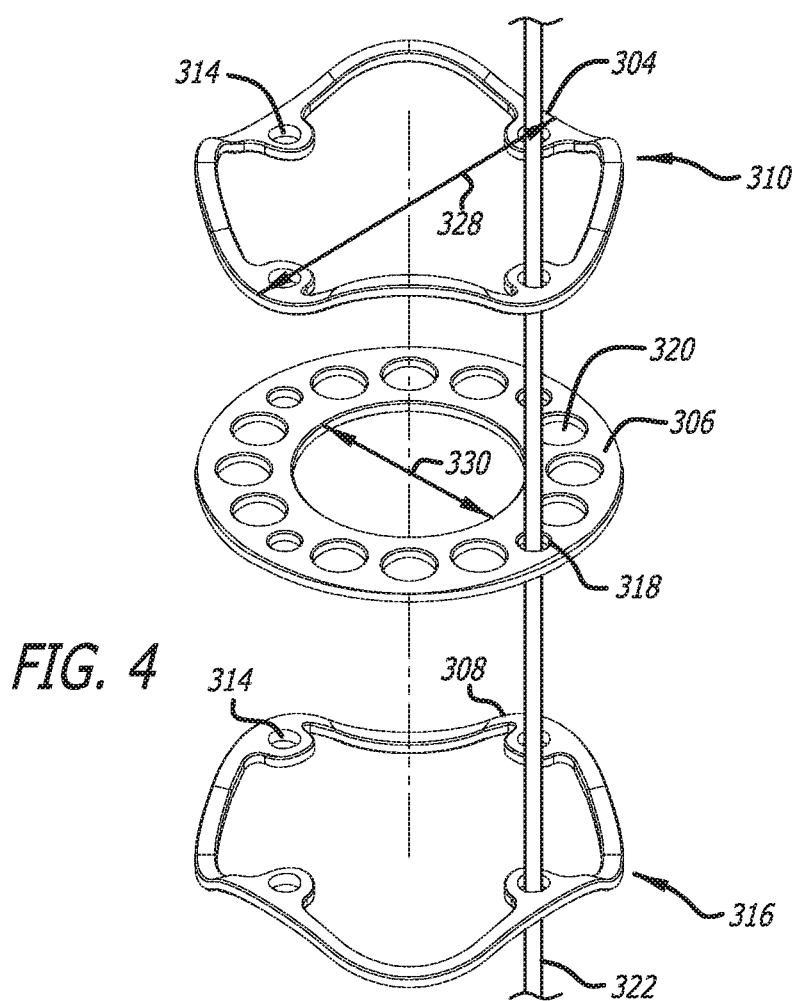
FIG. 4
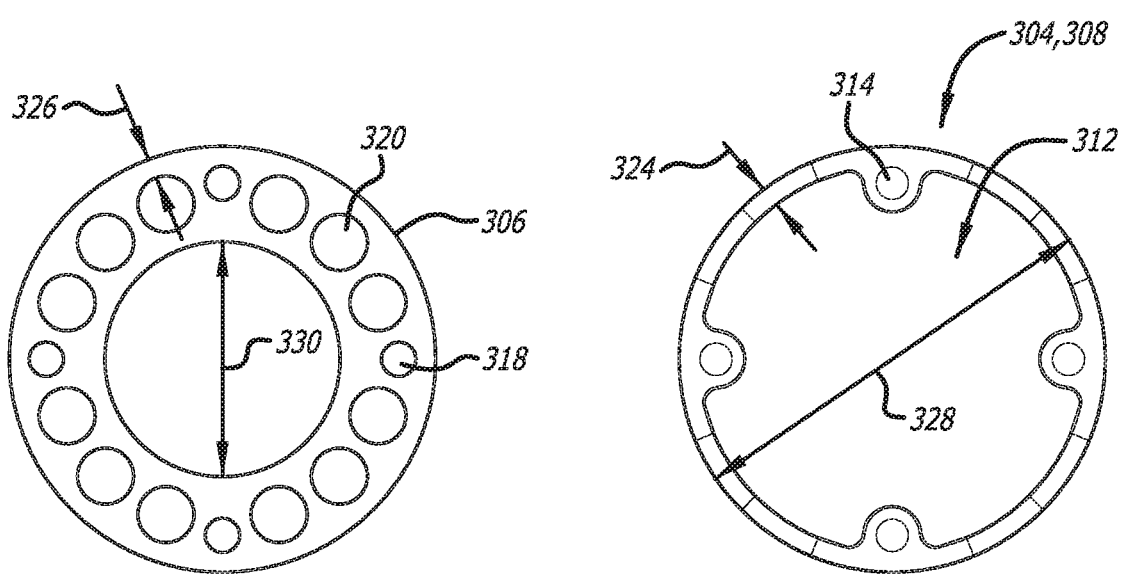
FIG. 5
FIG. 6

FLEXIBLE STRUCTURES

CROSS REFERENCE TO RELATED APPLICATIONS

This application is a national phase filing of International Application Number PCT/US2014/063546, filed Oct. 31, 2014, which claims the benefit of U.S. provisional patent application No. 61/898,281, filed Oct. 31, 2013, the entire disclosures each of which are incorporated herein by reference.

FIELD

The present disclosure provides flexible structures and frameworks comprising a plurality of at least one structural component useful for a variety of medical and non-medical applications.

SUMMARY

Flexible frameworks and structures are described herein and these terms may be used interchangeably. These frameworks include a plurality of at least one structural component having a waveform axially stacked and configured to form at least one internal conduit. In some embodiments, the frameworks can include an external coating or jacket. In other embodiment, non-waveform elements can be included in a framework.

In some embodiments, the structures or frameworks can be circular or noncircular structural components. If noncircular structural components are used, they can be in the form of rectangular strips with have a waveform. Such strips can be stacked while matching opposite waveform portions to create a framework. Thus, when circular or substantially circular components are described herein, these components can be replaced or substituted with noncircular components to create a framework.

In one embodiment, waveform gaps between two components provides flexibility because a waveform gap closes (e.g., flattens) and opens when acted upon. In some embodiments, no waveform gap (e.g., flat) may be present in a framework. In such a framework with no waveform gap, connections and/or links between two or more components may still be flexible because a waveform then forms between the two components when acted upon and returns to a flat condition when force is released. As such, in one embodiment, a waveform is not a prerequisite for flexibility.

Many different devices can be manufactured using the flexible frameworks described herein including medical devices such as catheters guide wires, artificial joints, articulating medical devices, endoscopes, steerable sheaths, laparoscopy devices, flexible cutter housings and bones, feeding tubes, and non-medical devices such as flexible fishing lures, actuatable mounts, articulating arms for instruments and camera systems, wire guides, and the like.

In some embodiments, the flexible frameworks can be elongated. However, in other embodiments, the length of a framework may be shorter than its diameter.

The flexible frameworks can include at least one non-wave element which can serve to add rigidity to the framework as well as internal conduits through its internal conduit hole(s). The non-wave elements can also provide a means for attachment of various other devices. The non-wave elements can define a functional cross section of a framework for through ports, lumens, wires/fiberoptics, cameras, combinations thereof, and the like. The non-wave elements can add mass and/or short non-steerable length to the flexible structure. Adding or removing non-wave elements can increase or decrease the steering radii of a flexible framework.

The plurality of at least one structural component can include repeat units of two, three, four, or more structural components. In some embodiments, the plurality includes repeat units of one structural component, one non-wave element and another structural component.

In some embodiments, each structural component is bonded to each non-wave element. In another embodiment, each structural component is bonded to adjacent non-wave elements and/or other structural components.

The frameworks can include at least one wire and compression spring combination configured to traverse at least one of the at least one internal conduits. In other embodiments, the frameworks can include two or more wire and tension/compression spring combinations. Further, the frameworks can include at least one conduit tube traversing at least one of the at least one internal conduits. In other embodiments, the framework includes two, three, or more conduit tubes, The structural components can include at least one complete wave or waveform. In other embodiments, the waveform of a structural component can include two, three, four, five, or more complete waves.

The frameworks can include top plates which can simply be a non-wave element in some embodiments. The wire and compression spring combinations can be bonded to the top plate in order to provide a location to apply pressure, tension, or compression in order to steer the framework. Bonding methods can include welding, brazing, soldering, gluing, plating, combinations thereof, and the like. Plating can include methods where two or more components can be plated together.

Methods of forming flexible frameworks are also described. These methods can include bonding together repeat units of a first structural component, a non-wave element and a second structural component, wherein the first structural component and the second structural component include a waveform, and wherein the flexible framework includes at least one internal conduit.

In another embodiment, the methods can include stacking repeat units of a first structural component, a non-wave element and a second structural component, wherein the first structural component, the non-wave element and the second structural component include complimentary holes forming an internal conduit. Then, at least one wire and tension and/or compression spring combination can be fed through the flexible framework and anchored to a top plate.

BRIEF DESCRIPTION OF THE DRAWINGS

FIG. 4 illustrates a perspective exploded view of the components making up the framework of FIG. 3.

FIG. 5 illustrates a plan view of the non-wave element utilized in the framework of FIG. 3.

FIG. 6 illustrates a plan view of the structural component utilized in the framework of FIG. 3.

DETAILED DESCRIPTION

Described herein are flexible structures and frameworks formed from two or more structural components forming a framework. In some embodiments, the framework is elongated. The structural components can form individual layers joined together to provide flexibility to the framework. The flexibility can be changed by, for example, changing the structural component materials, thickness of structural components, and or the distance between two joining points between adjacent components.

These flexible frameworks can be used to for medical devices as well as non-medical devices. Devices can include medical devices such as catheters, guide wires, artificial joints and bones, feeding tubes, endoscopes, steerable sheaths, steerable catheters, laparoscopy devices, combinations thereof, and the like can include flexible frameworks as described. Further, non-medical devices can include flexible frameworks as described, such as fishing lures, actuatable mounts, camera systems, wire guides, and the like.

Figure 1:
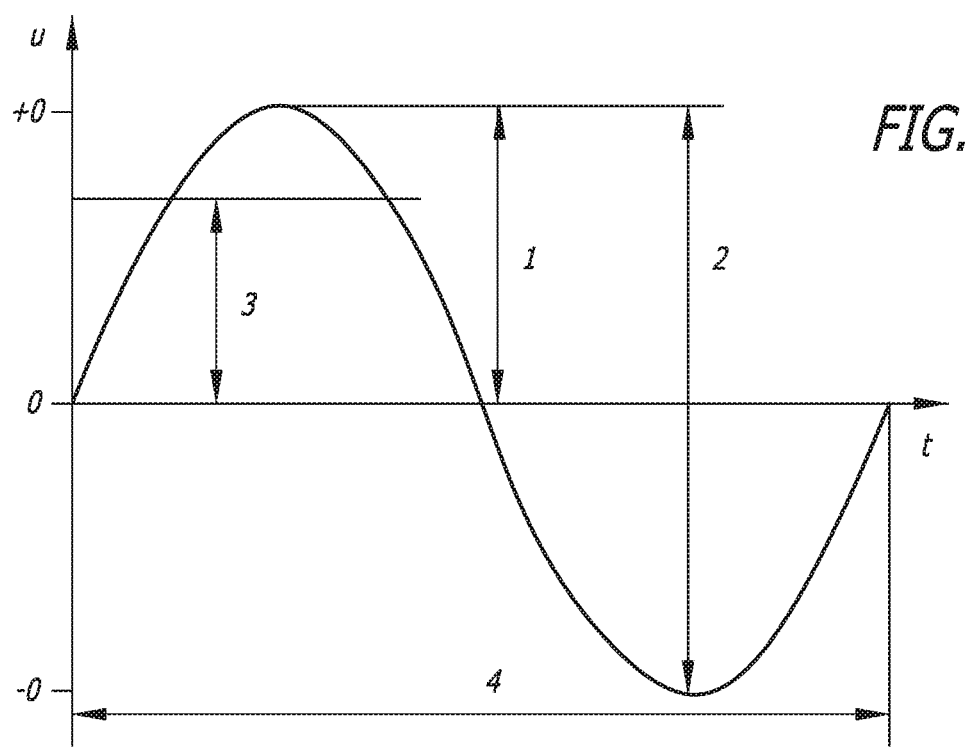
FIG. 1 illustrates a waveform of a structural component.

The structural components can have a shape of a radial wave including amplitude (wave height) and spatial frequency or period (number of oscillations or cycles) and radial wavelength. Waveforms can be sinusoidal, square, triangular, or other desired geometries. In some embodiments, a waveform may not be required for flexibility and may not be included. In one example embodiment, a structural component can be represented by a sinusoidal curve as illustrated in FIG. 1. FIG. 1 includes properties such as peak amplitude (1), peak-to-peak amplitude (2), RMS amplitude (3), and wave period (4). The curve of FIG. 1 is a basic waveform. Structural components can be formed with different geometries that can change the shape of this curve and hence the properties. For example, each wave can have equal or unequal wave periods with equal or unequal amplitudes. Such properties can be based on the desired functional shape and performance characteristics of an assembled framework.

Each structural element can have a circular shape. In other embodiments, structural elements can be square, rectangular, trapezoidal, triangular, or a combination thereof including circular. In some embodiments, different shaped structural elements can be combined to give uniquely shaped flexible structures. In one embodiment, the shape can be a half circle, a round triangular shape, or the like. The shapes of structural components can also change along the length of a framework in order to provide different properties at different lengths of the frameworks. In some embodiments, the diameter (e.g., size) of each structural element can change along the length of a flexible structure creating a tapered/changing shape structure.

The flexible structures can include individual components, each of which may or may not have a waveform. The crest of each wave can be assembled so that it is in contact with a trough of the wave of an adjacent component. The mating wave crests/troughs can be individually attached to each other by any conventional manner. However, in some embodiments, it is also possible that individual components are not attached to each but are linked by means of tensile or compression members that contain and align the assembly of the individual components.

The mechanical properties of frameworks, structures, and components described herein can be infinite because the mechanical and material properties of each individual component that forms a structure or framework can be specified and created prior to assembly. For example, a change to one components mechanical and/or material property may change the mechanical properties of the entire framework.

The frameworks can include layered joints that can change the flexibility of the entire structure. The flexibility of a framework can be modeled using finite element analysis to predict or determine mechanical properties of the assembled framework.

The joint distance can vary depending on desired framework properties. Joint distances can be about 1 μm, about 5 μm, about 10 μm, about 20 μm, about 30 μm, about 40 μm, about 50 μm, about 60 μm, about 70 μm, about 80 μm, about 90 μm, about 100 μm, about 200 μm, about 300 μm, about 400 μm, about 500 μm, about 600 μm, about 700 μm, about 800 μm, about 900 μm, about 1 mm, about 5 mm, about 1 cm, about 10 cm, about 50 cm, about 1 m, about 2 m, about 3 m, about 4 m, about 5 m, about 10 m, about 50 m, about 100 m, at most about 100 m, at most about 100 cm, at most about 1 cm, at most about 1 mm, between about 1 μm and about 1 cm, between about 1 μm and about 1 m, between about 1 cm and about 1 m, or between about 1 mm and about 100 m.

Material thickness can also vary depending on desired framework properties. Material thickness can be about 0.5 μm, about 1 μm, about 5 μm, about 10 μm, about 20 μm, about 30 μm, about 40 μm, about 50 μm, about 60 μm, about 70 μm, about 80 μm, about 90 μm, about 100 μm, about 200 μm, about 300 μm, about 400 μm, about 500 μm, about 600 μm, about 700 μm, about 800 μm, about 900 μm, about 1 mm, about 5 mm, about 1 cm, about 10 cm, about 50 cm, about 1 m, about 2 m, about 3 m, about 4 m, about 5 m, about 10 m, about 50 m, about 100 m, at most about 100 m, at most about 100 cm, at most about 1 cm, at most about 1 mm, between about 1 μm and about 1 cm, between about 1 μm and about 1 m, between about 1 cm and about 1 m, or between about 1 mm and about 100 m. In one embodiment, thickness can be about 0.127 mm (about 0.005 in).

Some of the mechanical and material properties that can be specified to change the performance of the individual components and thus the assembled structure can be, but are not limited to: base material composition (e.g., metallic or polymer, modulus of elasticity); heat treatment of the base material for strength; durometer; material thickness; wave height; number of waves; sectional moment of inertia; coatings; tensile strength of members; compressive strength of members; and the like. The combination of the various mechanical, material properties and design of the individual components creates a framework unique to itself and expands exponentially to the number of possible combinations. Component cross-sectional design, inside dimension, outside dimensions, and wall thickness can also determine mechanical properties of a given framework.

Each component described herein can be formed of a metal or metal alloy, a polymer, or a combination thereof. In some embodiments, components can be metallic coated with a polymer.

Metals and metal alloys can include, but are not limited to steel, stainless steel, super alloys, nitinol, iron, aluminum, brass, magnesium, boron, gold, silver, titanium, cobalt, scandium, vanadium, nickel, gallium, yttrium, rhodium, cadmium, indium, tin, platinum, tungsten, copper, titanium, barium, combinations thereof, and alloys thereof. In one embodiment, components can be formed of stainless steel.

Suitable polymers can include, but are not limited to poly(L-lactic acid), polycaprolactone, poly(lactide-co-glycolide), poly(ethylene-vinyl acetate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly(ether-esters) (e.g., PEO/PLA), polyurethanes, silicones, polyesters, polyolefins, polyisobutylene and ethylene-alphaolefin copolymers, acrylic polymers and copolymers, ethylene-co-vinylacetate, polybutylmethacrylate, vinyl halide polymers and copolymers (e.g., polyvinyl chloride), polyvinyl ethers (e.g., polyvinyl methyl ether), polyvinylidene halides (e.g., polyvinylidene fluoride and polyvinylidene chloride), polyacrylonitrile, polyvinyl ketones, polyvinyl aromatics (e.g., polystyrene), polyvinyl esters (e.g., polyvinyl acetate), acrylonitrile-styrene copolymers, ABS resins, polyamides (e.g., Nylon 66 and polycaprolactam), polycarbonates, polyoxymethylenes, polyimides, PET, polyethers, polyurethanes, rayon, cellophane, and carboxymethyl cellulose.

In some embodiments, suitable polymers can be selected from polyether block amides, thermoplastic elastomers such as a rubber, polybutylene terephthalate, styrene elastomers, hytrel, polyester elastomers, or combinations thereof.

In one embodiment, a suitable polymer can be a polyether block amide.

In one embodiment, a jacket or coating can be formed of a thermoplastic elastomer.

In one embodiment, a suitable polymer can be a polybutylene terephthalate (PBT).

In one embodiment, a suitable polymer can be a styrene elastomer.

In one embodiment, a suitable polymer can be a HYTREL® polymer (DuPont).

In one embodiment, a suitable polymer can be a polyester elastomer.

The mechanical characteristics of structural components can be directly influenced by several material and physical characteristics such as, but not limited to, base material selection, modulus of elasticity, hardness/heat treatment, length of the wave section in bending, height of the wave, cross sectional shape of the wave (for example, round, rectangular, square, trapezoidal, etc.) in bending about the Y-axis, and the like. For a given load, either tension or compression of an element can deflect accordingly. For structural components having substantially rectangular cross-sections, such as the example structural component cross-section in FIG. 2, the structural component's reaction to a given load is based on the Moment of Inertia about the Y-axis which is represented by $I_Y=\frac{1}{3}A^3B$. The height and width of the cross sectional area can be changed to directly affect the element and the overall assembled structure mechanical characteristics to achieve a specific design characteristic.

Figure 2:
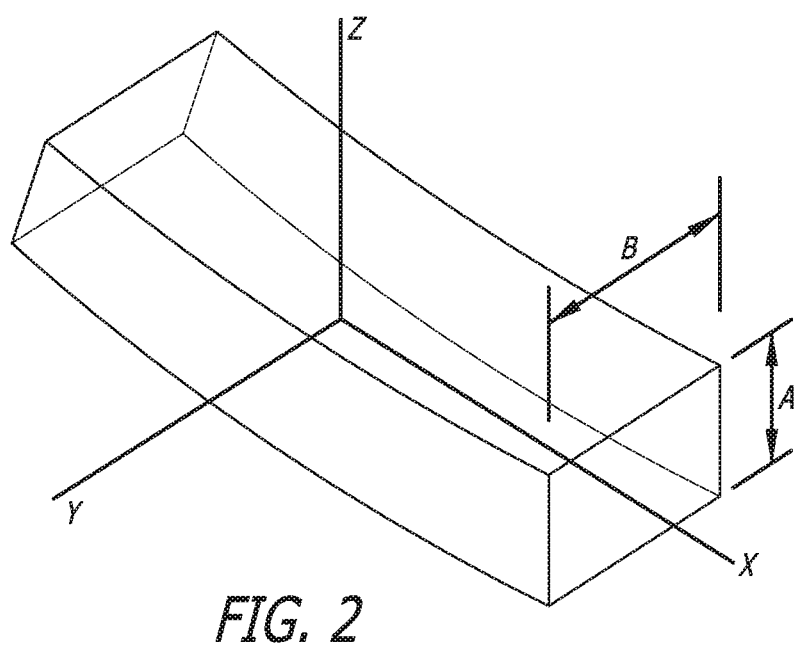
FIG. 2 illustrates a cross-section of a structural component.

As a non-limiting example, using a metal such as stainless steel, a rectangular cross-section (FIG. 2), a fixed wave height, and both fixed width ((B), FIG. 2) and height ((A), FIG. 2) can be varied to give various tensile strengths or resistances to bending.

In some embodiments, each individual structural component can have varied physical characteristics to alter the characteristics of the flexible structure. For example, the cross-sectional width of a structural component can be varied between waves of a single component such that one wave is wider than the next. Likewise, the thickness of a wave section can be varied such that a thinner wave can be more flexible than a thicker one. Further, the width or thickness of each wave can be varied within the wave itself the change the flexibility of the assembled structure at various angles of bending.

Combinations of individual structural components, each with unique physical characteristics, can be infinitely combined to change and influence the physical properties of the assembled flexible structure. As an example, a matrix of a single material, such as 304L stainless steel, and with consideration of only two physical properties, moment of inertia(s) ($I_Y=\frac{1}{3}A^3B$) and yield strength(s)/tensile strength (s), individual elements, each with unique physical properties can be created. Adding an additional variable to the matrix substantially increases the number of combinations of individual component properties. Thus, there can be many different physical properties that can be combined.

In some embodiments, yield strength, tensile strength, and/or bending resistances of the flexible structures can be altered by heat treating a metal, work hardening a metal, and/or annealing a metal used to form structural components. In other embodiments, yield strength, tensile strength, and/or bending resistances can be altered by applying a polymer coating to a metal structural component. Any of the polymers described herein can be used to coat a metal structural component.

Based on individual structural components, each with unique physical properties, frameworks can be designed that have different properties by simply changing the individual structural component properties. When considering combinations of just yield strength(s) of 100 kpsi, 150 kpsi, 175 kpsi, 200 kpsi, and 250 kpsi, and a fixed height/thickness (A) and width (B), five individual structural components can be created, each structural components having a unique and/or different physical property than another. If, for example, a third property is applied/injected, height/thickness (A) of 0.002 in, 0.003 in, 0.004 in, 0.005 in, and 0.006 in, 25 structural components, each having a unique and/or different physical property than another are created. For example, using only these 25 structural components to create a 25 structural component flexible structure, the combinations of each of these individual structural components can be assembled as factorial combination thereof. Such framework designs can allow an artisan to fine tune framework properties such as, but not limited to, bending, torsion, compression and tension by incrementally changing the various physical properties of individual structural components and the combinations of individual structural components.

This fine tuning is not found in commercially available continuously braided structures or extruded tubing where structural properties are generally homogeneous along the length of the structure or can only be practically changed by changing the polymer coating and/or braid density.

The design of a framework may not limit the cross sectional shape of a product requiring a flexible structure or joint and various features can be designed into the cross section of the structure creating through or closed lumens for other components while still maintaining the flexible structure.

In some embodiments, a framework of identical individual structural components can be combined to create a structure with consistent physical properties along the entire length of the structure. To change the properties of a multi-element structure along the length, the properties of one or more individual elements can be changed to design a multi-element structure with certain desirable characteristics which change along its length.

Based on the design of the structure, it may or may not be necessary to join the individual components. Individual elements can be joined together where the apex of the structures contact each other and can be accomplished by various mechanical or chemical means such as fasteners, wires, adhesives, solder, welding, brazing, plating, diffusion bonding, and the like, or combinations thereof. In some embodiments, the layers do not need to be joined.

In addition, flexible structures with unique cross-sections can be created by adding other structural components, e.g., non-wave elements, intermediate rings, spacers, washers, and the like, with different functional purposes to the flexible structure. These unique structural components when assembled into a structure create a flexible structure of continuous pathways or conduits for conductor wires, fiber optics, guide wires or any other mechanical or electrical device and are configured to attach/integrate a mechanical, electromechanical or electrical device to the structure.

Figure 3:
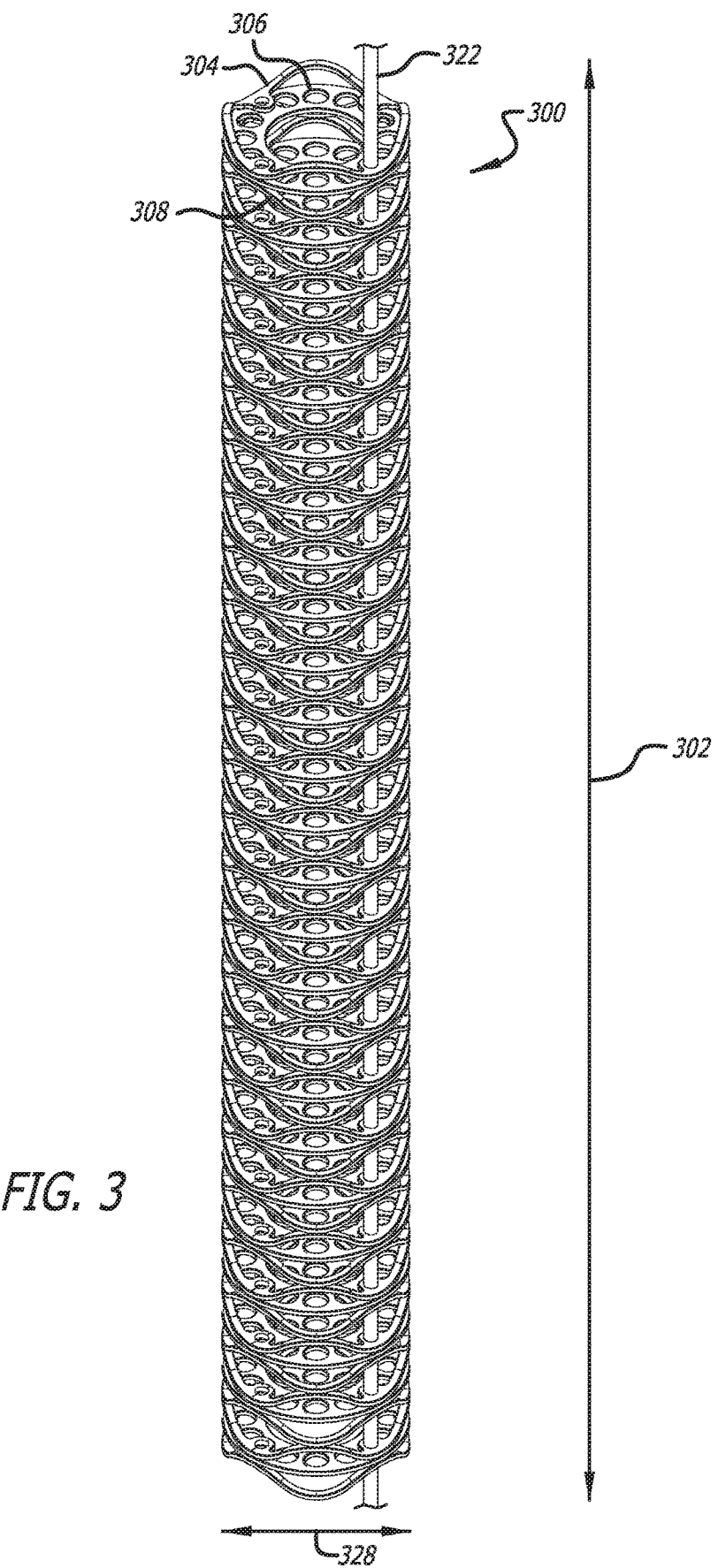
FIG. 3 illustrates a first example flexible framework.

An example framework 300 is illustrated in FIG. 3. Framework 300 has a length 302. Length 302 can vary depending on the particular application of the framework. Length 302 can be about 0.01 mm, about 0.05 mm, about 0.1 mm, about 0.05 mm, about 1 mm, about 5 mm, about 1 cm, about 10 cm, about 50 cm, about 1 m, about 2 m, about 3 m, about 4 m, about 5 m, about 10 m, about 50 m, about 100 m, between about 0.01 mm and about 1 cm, between about 0.1 mm and about 1 cm, between about 1 cm and about 1 m, between about 10 cm and about 1 m, or between about 1 mm and about 100 m.

Framework 300 can be formed of an upward component 304, a spacer and/or non-wave element 306, and a downward component 308. As illustrated in FIG. 4, upward component 304 can have at least one upward protruding portion 310. In other embodiments, upward component 304 can have two, three, four five, six, seven, eight, nine, ten, eleven, twelve, 13, 14 or 15 upward protruding portions. In one example embodiment, upward component 304 can have four upward protruding portions 310. As illustrated in FIG. 6, upward component 304 can have a substantially circular cross-section with a central hole 312.

Upward component 304 can further include one or more holes along its perimeter on an opposite portion of a waveform from upward portion. In one embodiment, upward component 304 includes four holes 314 along the interior of its perimeter. Holes 314 can be configured to house a structural member (not illustrated). Holes 314, or any holes described herein, can have any shape that can accommodate coupling devices (e.g., coupling devices 322) as described. Shapes can include, but are not limited to squares, rectangles, triangles, trapezoids, ellipses, other curvilinear shapes, or the like, or a combination thereof. In some embodiments, different shaped holes can be used in different locations to accommodate different coupling devices.

Downward component 308 can be an upward component 304 flipped upside down so that upward protruding portions are now downward protruding portions 316. In other words, downward component 308 can be a mirror image of upward component 304. However, in some embodiments, the two components can be configured differently.

Non-wave element 306 can also have a substantially circular cross-section as illustrated in FIG. 5. When matched with an upward component and a downward component, non-wave element 306 can have at least one matching hole 318 that aligns with at least one hole of upward component 304 and downward component 308. Non-wave element 316 can further include at least one additional hole 320 that can be larger or smaller than matching hole 318. In some embodiments, non-wave element 306 can have two, three, four five, six, seven, eight, nine, ten, eleven, twelve, thirteen, fourteen or fifteen additional holes 320 along its perimeter or within its body. In one example embodiment, non-wave element 306 has twelve additional holes 320 within its body.

To form a framework 300, the described components can be stacked and optionally joined and/or bonded. For example, as illustrated in FIG. 3, repeat units of upward component 304, stacked on a non-wave element 306, stacked on a downward component 308 can be stacked. Each touching point between the components can be bonded such as by welding (conventional, laser, resistance etc.), adhesives, diffusion bonding, soldering or any conventional or nonconventional means of joining the materials.

In other embodiments, no bonding may be required or only some of the touching points may be bonded. For example, one or more coupling devices 322 such as cables, wires, springs, coils or the like can be fed through a particular channel and bonded to a top and bottom spacer piece.

Referring to FIGS. 5 and 6, upward component 304 and downward component 308 can be configured such that width 324 is no larger than width 326 and additional holes 320 are not obstructed when components are stacked.

Structural outer diameter 328 can also vary depending on the application of the framework. Structural outer diameter 328 can be any shape that is conducive to the application of the framework. For example, structural outer diameter 328 can have a shape of a circle, ellipse, square, triangle, or any other curvilinear shape. Further, structural outer diameter 328 can be about 1 µm, about 5 µm, about 1 mm, about 5 mm, about 10 mm, about 100 mm, about 200 mm, about 500 mm, about 1 m, about 5 m, about 10 m, about 50 m, about 100 m, between about 1 µm and about 1 cm, between about 1 µm and about 1 m, between about 10 cm and about 1 m, or between about 1 mm and about 100 m.

Structural inner diameter 330 can also vary depending on the application of the framework. Structural inner diameter 330 can be the smallest diameter measurement when a structure is created, and it can be any shape that is conducive to the application of the framework. For example, structural inner diameter 330 can have a shape of a circle, ellipse, square, triangle, or any other curvilinear shape. Further, structural inner diameter 330 can be about 1 µm, about 5 µm, about 1 mm, about 5 mm, about 10 mm, about 100 mm, about 200 mm, about 500 mm, about 1 m, about 5 m, about 10 m, about 50 m, about 100 m, between about 1 µm and about 1 cm, between about 1 µm and about 1 m, between about 1 cm and about 1 m, or between about 1 mm and about 100 m. In framework 300, the structural inner diameter happens to be on non-wave element 306, but this need not be the case in all circumstances. In another embodiment, structural inner diameter may be on another component(s).

Figure 7:
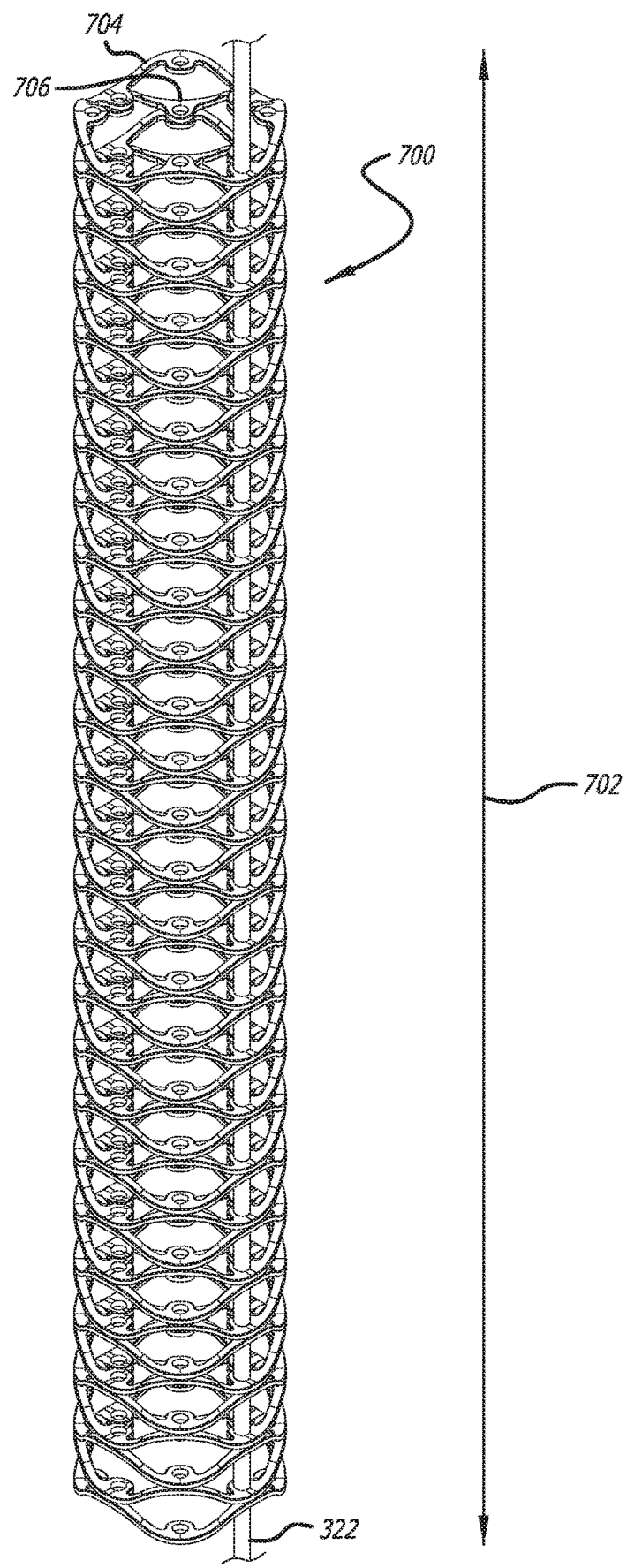
FIG. 7 illustrates another example flexible framework.

Another example framework 700 is illustrated in FIG. 7. Framework 700 has a length 702. Length 702 can vary depending on the particular application of the framework. Length 702 can be about 1 mm, about 5 mm, about 1 cm, about 10 cm, about 50 cm, about 1 m, about 2 m, about 3 m, about 4 m, about 5 m, about 10 m, about 50 m, about 100 m, between about 1 mm and about 1 cm, between about 1 cm and about 1 m, between about 10 cm and about 1 m, or between about 1 mm and about 100 m.

Figure 8:
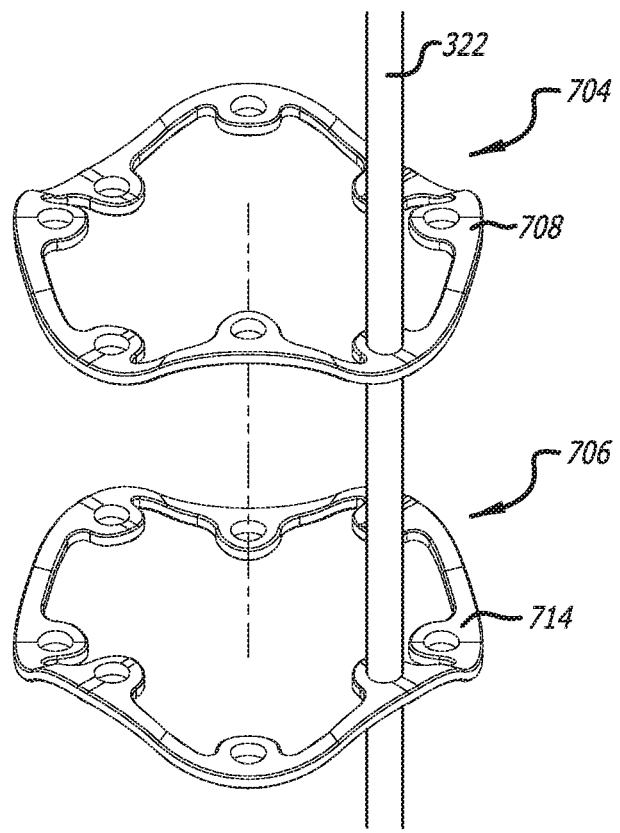
FIG. 8 illustrates a perspective exploded view of the components making up the framework of FIG. 7.
Figure 9:
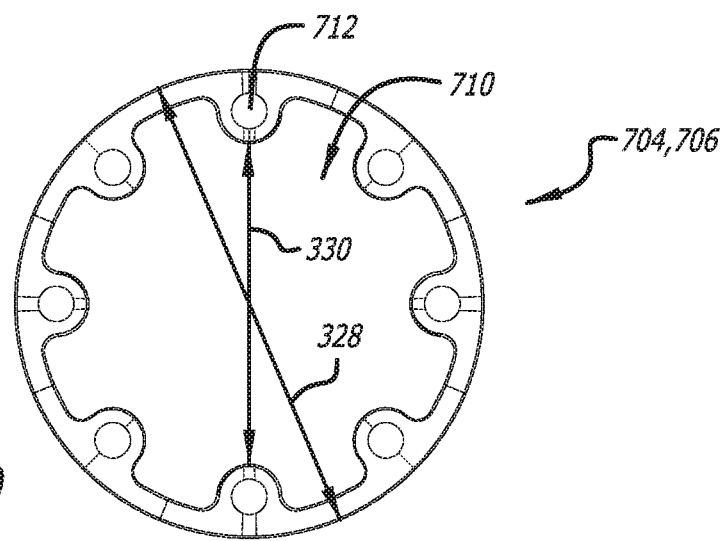
FIG. 9 illustrates a plan view of the structural component utilized in the framework of FIG. 7.

Framework 700 can be formed of a top component 704 and a bottom component 706. As illustrated in FIG. 8, top component 704 can have at least one upward protruding portion 708. In other embodiments, top component 704 can have two, three, four five, six, seven, eight, nine, ten, eleven, twelve, thirteen, fourteen or fifteen upward protruding portions. In one example embodiment, top component 704 can have four upward protruding portions 708. As illustrated in FIG. 9, top component 704 can have a substantially circular cross-section with a central hole 710.

Top component 704 can further include one or more holes along its perimeter on an opposite portion of a waveform from top portion. In one embodiment, top component 704 includes eight holes 712 along the interior of its perimeter. Holes 712 can be configured to house a structural member (not illustrated).

Bottom component 706 can be an top component 704 flipped upside down so that upward protruding portions are now downward protruding portions 714. In other words, bottom component 708 can be a mirror image of top component 704. However, in some embodiments, the two components can be configured differently.

In some embodiments, in order to form portions of a flexible structure from a stack of wave components such as top components 704, a top component 704 can be spun a single half-wave portion right or left in order to create a bottom component 706 and align the waveforms for assembly.

To form a framework 700, the described components can be stacked and optionally joined and/or bonded. For example, as illustrated in FIG. 7, repeat units of top component 704 stacked on a bottom component 706 can be stacked to join a continuous linear framework. Each touching point between the components can be bonded such as by welding (conventional, laser, resistance etc.), adhesives, diffusion bonding, soldering or any conventional or non-conventional means of joining the materials.

In other embodiments, no bonding may be required or only some of the touching points may be bonded. For example, one or more coupling devices 322 such as cables, wires, springs, coils, fiber optics, conductor wires, or the like can be fed through a particular channel and bonded to a top and bottom spacer piece. In one embodiment, these coupling devices 322 can be used to push and/or pull the framework.

Structural outer diameter 328 can also vary depending on the application of the framework. Structural outer diameter 328 can be any shape that is conducive to the application of the framework. For example, structural outer diameter 328 can have a shape of a circle, ellipse, square, triangle, or any other curvilinear shape. Further, structural outer diameter can be 328 can be about 1 µm, about 5 µm, about 1 mm, about 5 mm, about 10 mm, about 100 mm, about 200 mm, about 500 mm, about 1 m, about 5 m, about 10 m, about 50 m, about 100 m, between about 1 µm and about 1 cm, between about 1 µm and about 1 m, between about 1 cm and about 1 m, or between about 1 mm and about 100 m.

Structural inner diameter 330 can also vary depending on the application of the framework. Structural inner diameter 330 is the smallest diameter measurement when a structure is created, and it can be any shape that is conducive to the application of the framework. For example, structural inner diameter 330 can have a shape of a circle, ellipse, square, triangle, or any other curvilinear shape. Further, structural inner diameter can be 330 can be about 1 µm, about 5 µm, about 1 mm, about 5 mm, about 10 mm, about 100 mm, about 200 mm, about 500 mm, about 1 m, about 5 m, about 10 m, about 50 m, about 100 m, between about 1 µm and about 1 cm, between about 1 µm and about 1 m, between about 1 cm and about 1 m, or between about 1 mm and about 100 m.

Figure 10:
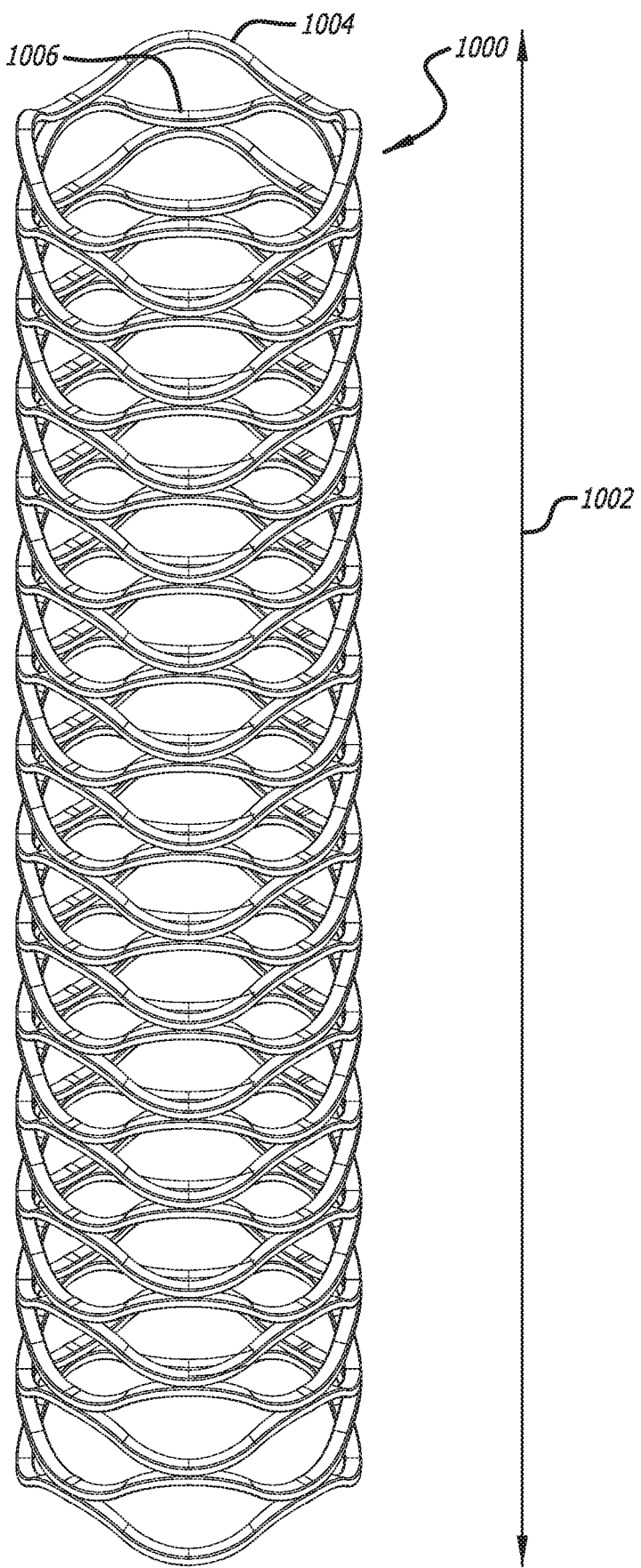
FIG. 10 illustrates another example flexible framework.

Another example framework 1000 is illustrated in FIG. 10. Framework 1000 has a length 1002. Length 1002 can vary depending on the particular application of the framework. Length 1002 can be about 1 mm, about 5 mm, about 1 cm, about 10 cm, about 50 cm, about 1 m, about 2 m, about 3 m, about 4 m, about 5 m, about 10 m, about 50 m, about 100 m, between about 1 mm and about 1 cm, between about 1 cm and about 1 m, between about 10 cm and about 1 m, or between about 1 mm and about 100 m.

Figure 11:
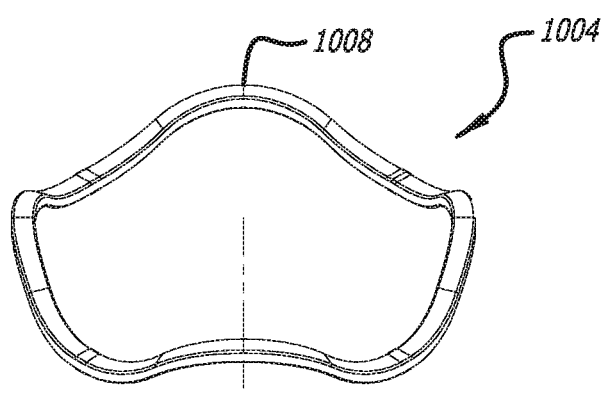
FIG. 11 illustrates a perspective exploded view of the components making up the framework of FIG. 10.
Figure 12:
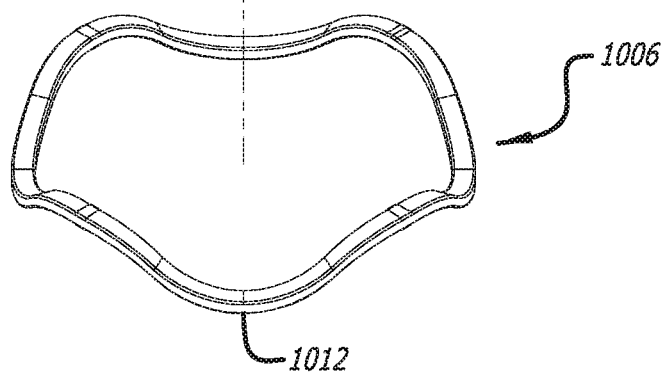
FIG. 12 illustrates a plan view of the structural component utilized in the framework of FIG. 10.
Figure 12:
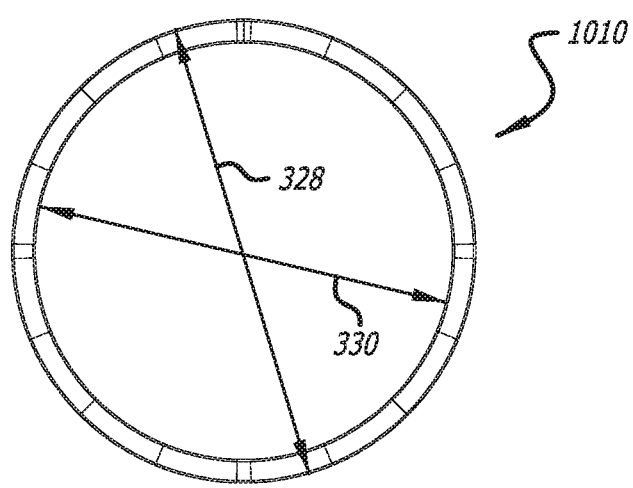

Framework 1000 can be formed of a first component 1004 and a second component 1006. As illustrated in FIG. 11, first component 1004 can have at least one upward protruding portion 1008. In other embodiments, first component 1004 can have two, three, four five, six, seven, eight, nine, ten, eleven, twelve, thirteen, fourteen or fifteen upward protruding portions. In one example embodiment, first component 1004 can have four upward protruding portions 1008. As illustrated in FIG. 12, both the top component 1004 and bottom component 1006 can have a substantially circular cross-section with a central hole 1010.

Second component 1006 can be a first component 1004 flipped upside down so that upward protruding portions are now downward protruding portions 1012. In other words, second component 1006 can be a mirror image of first component 1004. However, in some embodiments, the two components can be configured differently.

To form a framework 1000, the described components can be stacked and joined and/or bonded. For example, as illustrated in FIG. 10, repeat units of first component 1004 stacked on a second component 1006 can be stacked to join a continuous linear framework. Each touching point between the components is bonded by welding (conventional, laser, resistance etc.), adhesives, diffusion bonding, soldering or any conventional or non-conventional means of joining the materials, a combination thereof, or the like.

Structural outer diameter 328 can also vary depending on the application of the framework. Structural outer diameter 328 can be any shape that is conducive to the application of the framework. For example, structural outer diameter 328 can have a shape of a circle, ellipse, square, triangle, or any other curvilinear shape. Further, structural outer diameter can be 328 can be about 1 µm, about 5 µm, about 1 mm, about 5 mm, about 10 mm, about 100 mm, about 200 mm, about 500 mm, about 1 m, about 5 m, about 10 m, about 50 m, about 100 m, between about 1 µm and about 1 cm, between about 1 µm and about 1 m, between about 1 cm and about 1 m, or between about 1 mm and about 100 m.

Structural inner diameter 330 can also vary depending on the application of the framework. Structural inner diameter 330 is the smallest diameter measurement when a structure is created, and it can be any shape that is conducive to the application of the framework. For example, structural inner diameter 330 can have a shape of a circle, ellipse, square, triangle, or any other curvilinear shape. Further, structural inner diameter can be 330 can be about 1 µm, about 5 µm, about 1 mm, about 5 mm, about 10 mm, about 100 mm, about 200 mm, about 500 mm, about 1 m, about 5 m, about 10 m, about 50 m, about 100 m, between about 1 µm and about 1 cm, between about 1 µm and about 1 m, between about 1 cm and about 1 m, or between about 1 mm and about 100 m.

Figure 13:
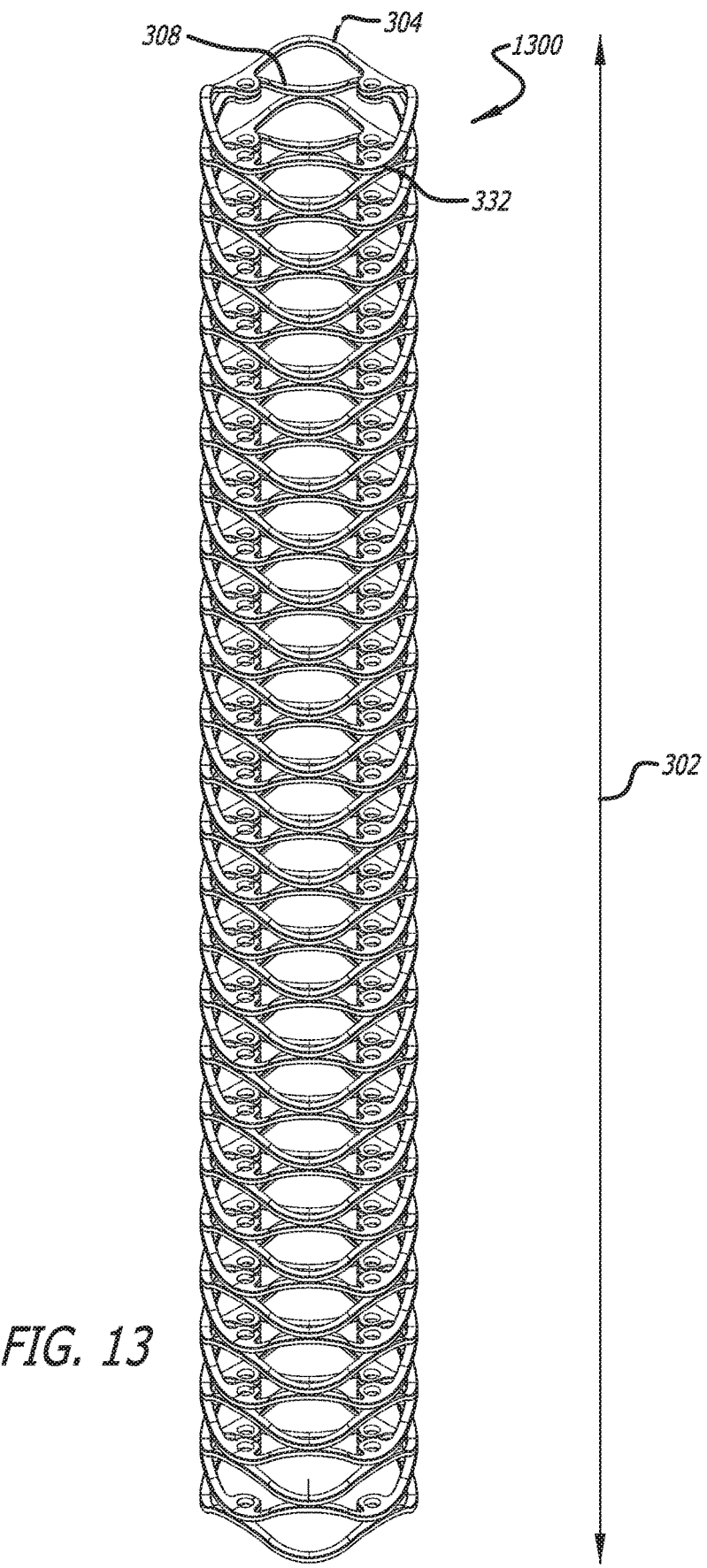
FIG. 13 illustrates another example flexible framework.
Figure 14:
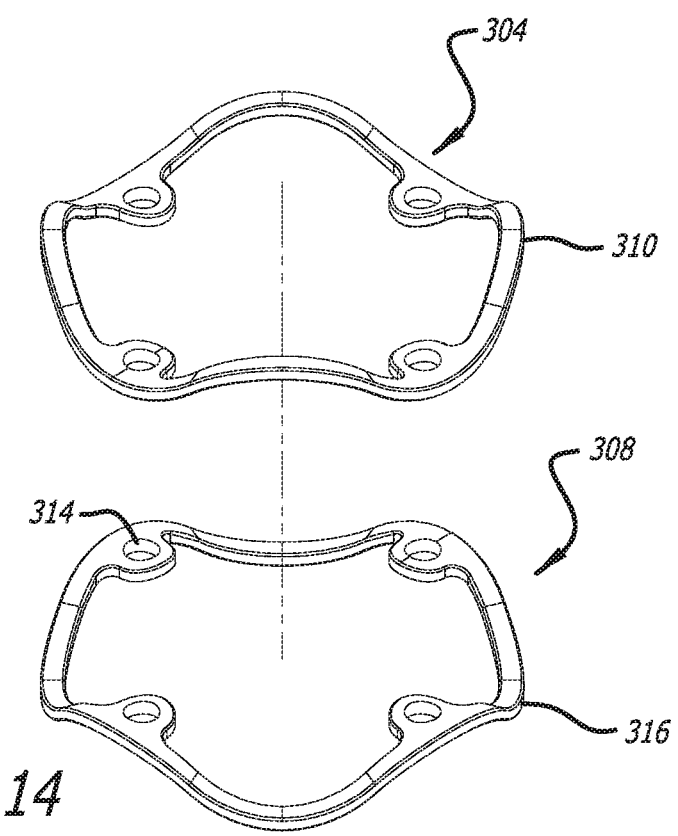
FIG. 14 illustrates a perspective exploded view of the components making up the framework of FIG. 13.
Figure 15:
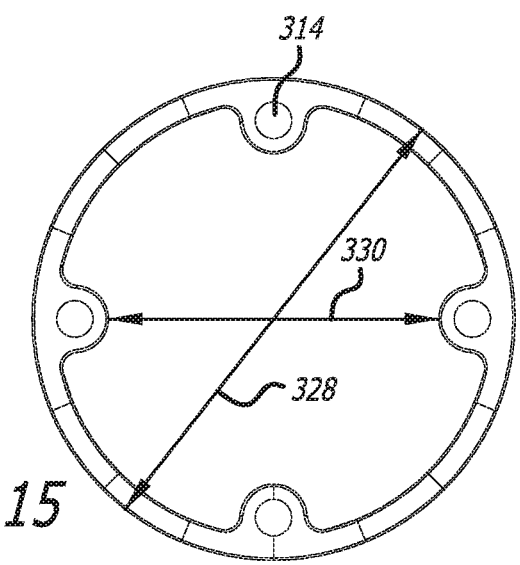
FIG. 15 illustrates a plan view of the structural component utilized in the framework of FIG. 13.

Another example framework 1300 is illustrated in FIGS. 13-15. Framework 1300 has a length 1302. Length 1302 can vary depending on the particular application of the framework. Length 1302 can be about 1 mm, about 5 mm, about 1 cm, about 10 cm, about 50 cm, about 1 m, about 2 m, about 3 m, about 4 m, about 5 m, about 10 m, about 50 m, about 100 m, between about 1 mm and about 1 cm, between about 1 cm and about 1 m, between about 10 cm and about 1 m, or between about 1 mm and about 100 m.

Similar to framework 300, framework 1300 can be formed of upward component 304 and a downward component 308, but without, a non-wave element 306. As illustrated in FIG. 14, upward component 304 can have at least one upward protruding portion 310 that in framework 1300 will not rest against a non-wave element but rather downward component 308.

Upward component 304 can include one or more holes along its perimeter on an opposite portion of a waveform from upward portion. In one embodiment, upward component 304 includes four holes 314 along the interior of its perimeter. Holes 314 can be configured to house a structural member (not illustrated).

Downward component 308 can be an upward component 304 flipped upside down so that upward protruding portions 304 are now downward protruding portions 316. In other words, downward component 308 can be a mirror image of upward component 304. However, in some embodiments, the two components can be configured differently.

Framework 1300 can include alternating component touching areas with holes 314 and without holes. Each touching point 332 between the components can be bonded such as by welding (conventional, laser, resistance etc.), adhesives, diffusion bonding, soldering or any conventional or non-conventional means of joining the materials, a combination thereof, or the like.

In other embodiments, no bonding may be required or only some of the touching points may be bonded. For example, one or more coupling devices (not illustrated) such as cables, wires, springs, coils or the like can be fed through a particular channel and bonded to a top and bottom spacer piece.

Structural outer diameter 328 can also vary depending on the application of the framework. Structural outer diameter 328 can be any shape that is conducive to the application of the framework. For example, structural outer diameter 328 can have a shape of a circle, ellipse, square, triangle, crescent like (e.g., having two ends of some ½ geometric shape) or any other curvilinear shape. Further, structural outer diameter 328 can be about 1 µm, about 5 µm, about 1 mm, about 5 mm, about 10 mm, about 100 mm, about 200 mm, about 500 mm, about 1 m, about 5 m, about 10 m, about 50 m, about 100 m, between about 1 µm and about 1 cm, between about 1 µm and about 1 m, between about 1 cm and about 1 m, or between about 1 mm and about 100 m.

Structural inner diameter 330 can also vary depending on the application of the framework. Structural inner diameter 330 is the smallest diameter measurement when a structure is created, and it can be any shape that is conducive to the application of the framework. For example, structural inner diameter 330 can have a shape of a circle, ellipse, square, triangle, or any other curvilinear shape. Further, structural inner diameter can be 330 can be about 1 µm, about 5 µm, about 1 mm, about 5 mm, about 10 mm, about 100 mm, about 200 mm, about 500 mm, about 1 m, about 5 m, about 10 m, about 50 m, about 100 m, between about 1 µm and about 1 cm, between about 1 µm and about 1 m, between about 1 cm and about 1 m, or between about 1 mm and about 100 m. In framework 300, the structural inner diameter happens to be on non-wave element 306, but this need not be the case in all circumstances. In other embodiment, structural inner diameter may be on another component(s).

Another example framework 1600 and its components are illustrated in FIGS. 16-19. Framework 1600 has a length 1602. Length 1602 can vary depending on the particular application of the framework. Length 1602 can be about 1 mm, about 5 mm, about 1 cm, about 10 cm, about 50 cm, about 1 m, about 2 m, about 3 m, about 4 m, about 5 m, about 10 m, about 50 m, about 100 m, between about 1 mm and about 1 cm, between about 1 cm and about 1 m, between about 10 cm and about 1 m, or between about 1 mm and about 100 m.

Figure 17:
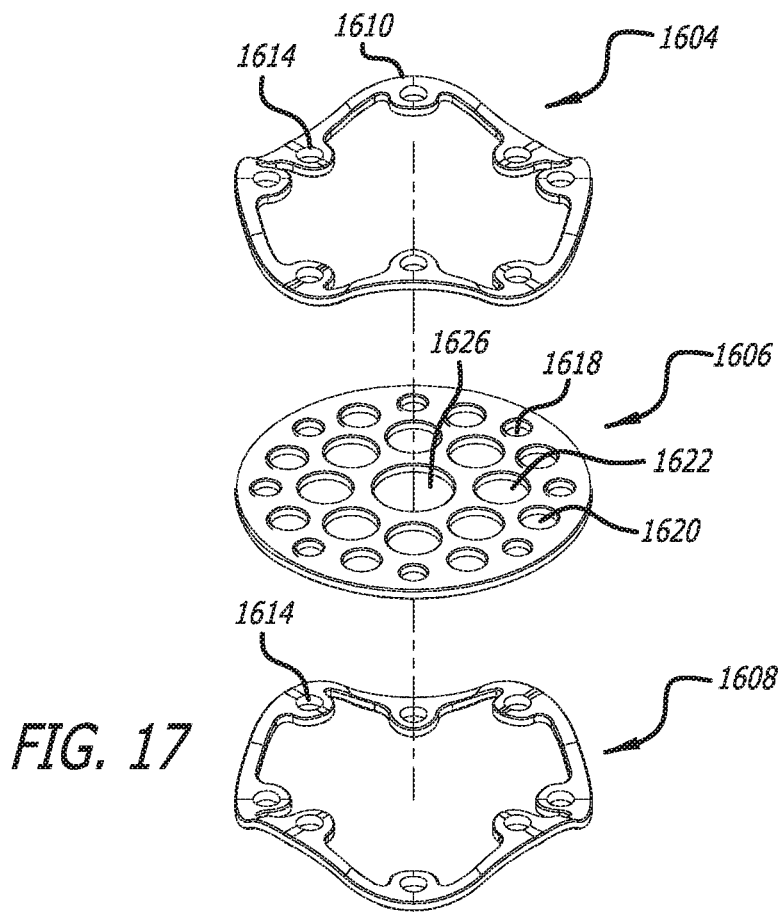
FIG. 17 illustrates a perspective exploded view of the components making up the framework of FIG. 16.
Figures 18, 19:
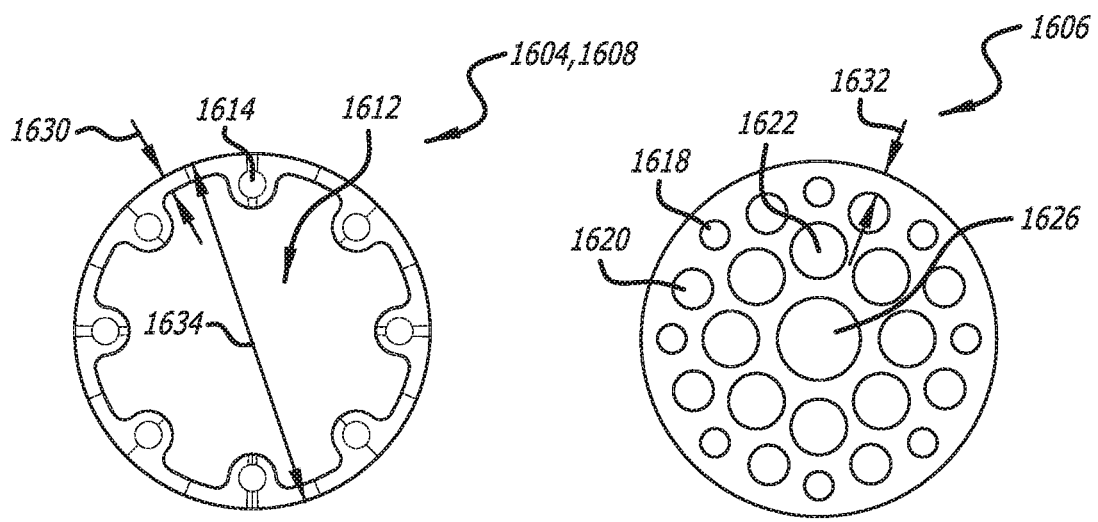
FIG. 18 illustrates a plan view of the structural component utilized in the framework of FIG. 16.
FIG. 19 illustrates a plan view of the non-wave element utilized in the framework of FIG. 16.

Framework 1600 can be formed of a first component 1604, a non-wave element 1606, and a second component 1608. As illustrated in FIG. 17, first component 1604 can have at least one upward protruding portion 1610. In other embodiments, first component 1604 can have two, three, four five, six, seven, eight, nine, ten, eleven, twelve, thirteen, fourteen or fifteen upward protruding portions. In one example embodiment, first component 1604 can have four upward protruding portions 1610. As illustrated in FIG. 18, first component 1604 can have a substantially circular cross-section with a central hole 1612.

First component 1604 can further include one or more holes 1614 along its perimeter with at least one on each waveform portion. In one embodiment, first component 1604 includes eight holes 1614 along the interior of its perimeter. Holes 1614 can be configured to house a structural member (not illustrated).

Second component 1608 can be a first component 1604 flipped upside down so that upward protruding portions 1610 are now downward protruding portions 1616 and end up mating with upward protruding portions 1610. In other words, second component 1608 can be a mirror image of first component 1604. However, in some embodiments, the two components can be configured differently.

Non-wave element 1606 can also have a substantially circular cross-section as illustrated in FIG. 19. When matched with a first component and a second component, non-wave element 1606 can have at least one matching hole 1618 that aligns with at least one hole of first component 1604 and second component 1608. Non-wave element 1606 can further include at least one additional perimeter hole 1620 that can be larger or smaller than matching hole 1618. In some embodiments, non-wave element 1606 can have two, three, four five, six, seven, eight, nine, ten, eleven, twelve, thirteen, fourteen or fifteen additional perimeter holes 1620 along its perimeter or within its body. In one example embodiment, non-wave element 1606 has eight additional perimeter holes 1620 within its body.

Further, non-wave element 1606 can include at least one channel hole 1622 that with other non-wave elements can form a channel 1624 axially along framework 1600. In one embodiment, non-wave element 1606 can include eight channel holes resulting in a framework with eight channels.

Further still, non-wave element 1606 can include a central hole 1626 that with other non-wave elements can form a central channel 1628 axially through framework 1600. Central channel 1628 can have a diameter that can be any shape that is conducive to the application of the framework. For example, central channel 1628 can have a shape of a circle, ellipse, square, triangle, or any other curvilinear shape. Further, central channel 1628 can have a diameter of about 1 μm, about 5 μm, about 1 mm, about 5 mm, about 10 mm, about 100 mm, about 200 mm, about 500 mm, about 1 m, about 5 m, about 10 m, about 50 m, about 100 m, between about 1 μm and about 1 cm, between about 1 μm and about 1 m, between about 1 cm and about 1 m, or between about 1 mm and about 100 m.

Figure 16:
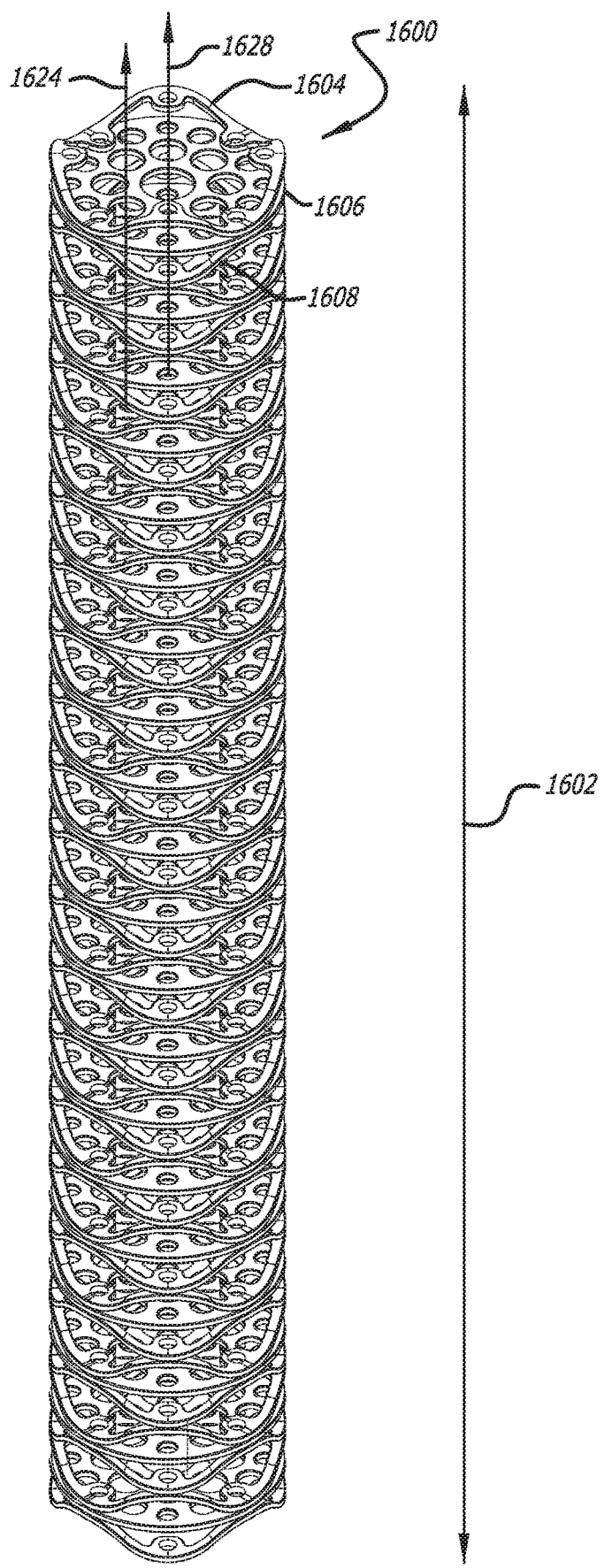
FIG. 16 illustrates another example flexible framework.

To form a framework 1600, the described components can be stacked and optionally joined and/or bonded. For example, as illustrated in FIG. 16, repeat units of first component 1604, stacked on a spacer ring 1606, stacked on a second component 1608 can be stacked. Each touching point between the components can be bonded such as by welding (conventional, laser, resistance etc.), adhesives, diffusion bonding, soldering, plating or any conventional or non-conventional means of joining the materials, a combination thereof, or the like.

In other embodiments, no bonding may be required or only some of the touching points may be bonded. For example, one or more coupling devices such as cables, wires, springs, coils or the like can be fed through a particular channel and bonded to a top and bottom spacer piece.

Referring to FIGS. 18 and 19, first component 1604 and second component 1608 can be configured such that width 1630 is no larger than width 1632 and additional holes 1620 are not obstructed when components are stacked.

Structural outer diameter 1634 can also vary depending on the application of the framework. Structural outer diameter 1634 can be any shape that is conducive to the application of the framework. For example, structural outer diameter 1634 can have a shape of a circle, ellipse, square, triangle, crescent like (e.g., having two ends of some ½ geometric shape) or any other curvilinear shape. Further, structural outer diameter can be 1634 can be about 1 μm, about 5 μm, about 1 mm, about 5 mm, about 10 mm, about 100 mm, about 200 mm, about 500 mm, about 1 m, about 5 m, about 10 m, about 50 m, about 100 m, between about 1 μm and about 1 cm, between about 1 μm and about 1 m, between about 1 cm and about 1 m, or between about 1 mm and about 100 m.

Figure 20:
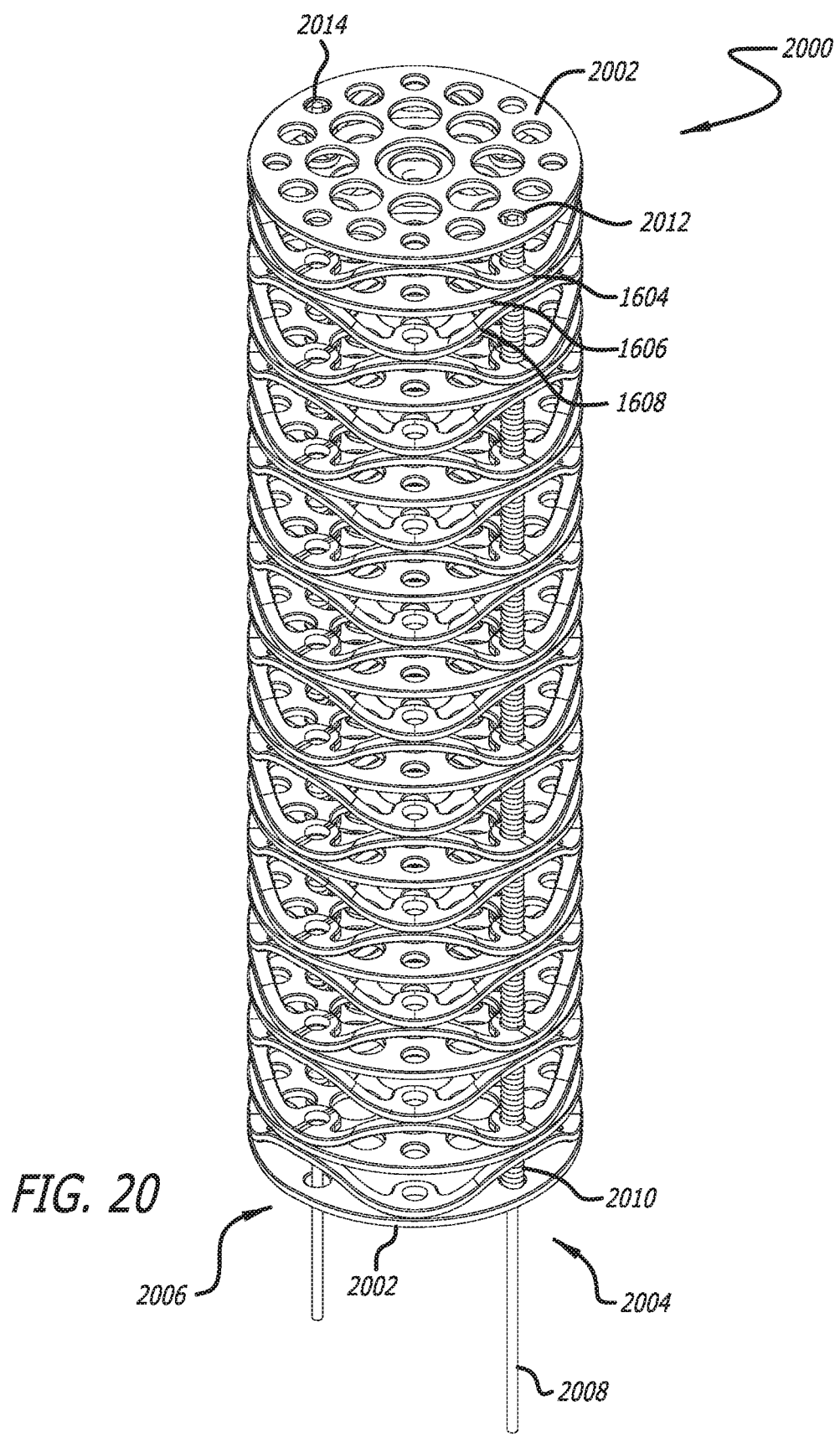
FIG. 20 illustrates the flexible framework of FIG. 16 including a top plate and wire and tension spring combinations.

FIG. 20 illustrates a framework similar to that of FIG. 16 with an anchor plate 2002 attached to the top of framework 1600 and a bottom anchor plate 2024 at the bottom of framework 1600. In some embodiments, anchor plate 2002 can simply be a repurposed non-wave element. In other embodiments, anchor plate 2002 and bottom anchor plate 2024 are the same. Here, anchor plate 2002 is non-wave element 1606.

One or more coupling devices as described herein can be fed though a given channel and bonded to anchor plate 2002. In FIG. 20 as an example, first coupling device 2004 and second coupling device 2006 each include wire 2008 covered by spring 2010. Spring 2010 can be an overcoil which provides compression strength to wire 2008. First coupling device 2004 can be anchored to anchor plate 2002 at hole 2012 using, for example a weld. Similarly, second coupling device 2006 can be anchored to anchor plate 2002 at hole 2014 using, for example a weld.

Spring 2010 can terminate at bottom anchor plate 2024. Thus between anchor plates, a spring can retain a particular tension or compression. Likewise, any hole in a structural element can be made smaller than the spring but larger than a wire to terminate the travel of a spring. Other terminations can be used in conjunction with the flexible structures described.

Using a device connected to the opposite ends of first coupling device 2004 and second coupling device 2006 from the welds, each of the coupling devices can be independently pulled thereby compressing that particular side of the framework and "steering" the device. Framework 2000 in FIG. 20 includes eight perimeter holes in anchor plate 2002 that form channels through the entire framework that can house a coupling device. As such, using these eight channels the framework can be compressed and hence steered in a combination of eight independent directions.

In some embodiments, closed coil springs can prevent steering and/or open coil springs can allow a fixed amount of steering limited by a total open space of the coil. In some embodiments, closed coil springs can be positioned along a flexible structure to prevent steering in one plane but not in the 90 degree plane. For example, a steering member can include portions of both compressive and tensile springs to allow different movements to different portions of the frameworks described. In still other embodiments, only portions may have springs present and other portions may not have springs at all.

Components can be included in the design of a framework as described in order to add mechanical articulation, tension, and/or compression constraints. The framework of FIG. 20 can utilize tension and compression by incorporating, for example, a tension spring with an internal wire, and positioned 180° from the tension spring is a compression spring, also with a internal wire.

Manipulation of this framework can be accomplished by applying tension on the wire internal to the compression spring, causing the structural components on the side of the compression spring to compress which shortens the length of the framework on that side, bending the structure. In this design the compression spring can also function as a manipulation limiter as once the compression spring is fully compressed the structure is no longer capable of being manipulated. If tension is applied to the internal wire in the tension spring, the framework will not react as that side of the structure is not able to compress. Applying a compression load to the internal wire in the tension spring will cause manipulation of the structure, limited by the compression of the compression spring 180° away.

Figure 21:
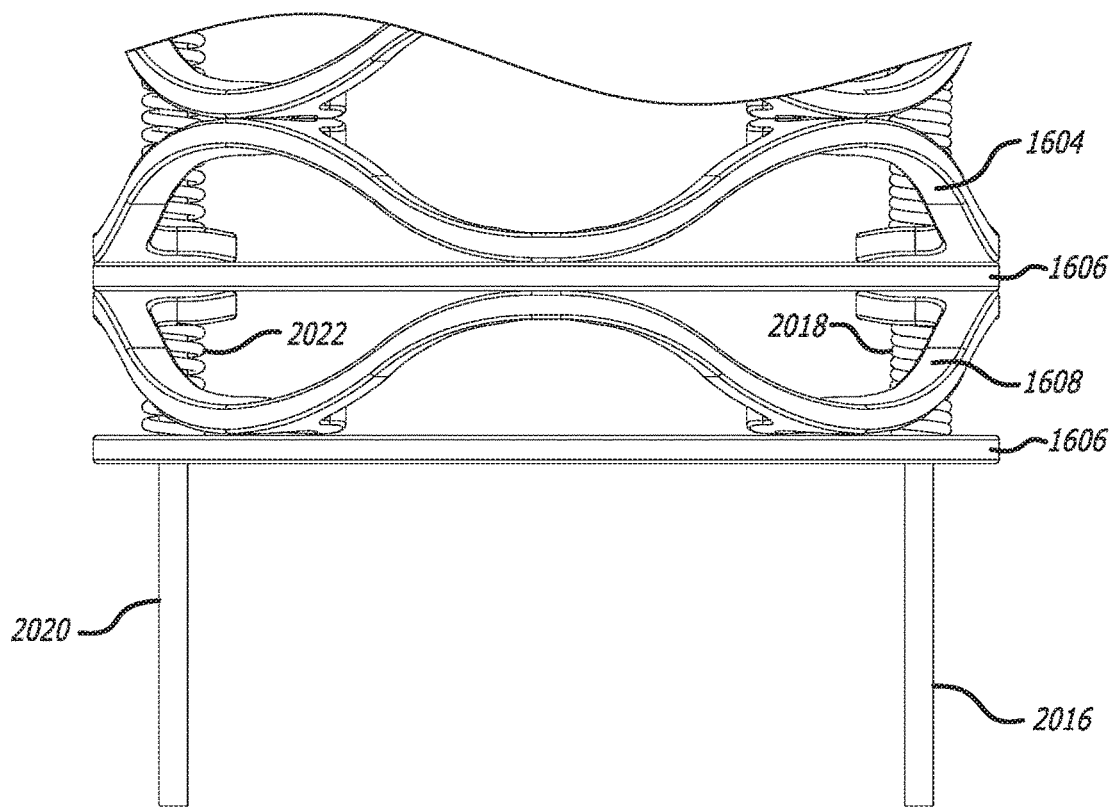
FIG. 21 illustrates a zoomed view of wire, tension and compression spring combination.

In one embodiment, as illustrated in FIG. 21, first wire 2016 is covered by compressed spring 2018. Compressed spring 2018 can be an overcoil which provides compressed strength to first wire 2016 thereby preventing further compression. Second wire 2020 is covered by relaxed spring

2022. Relaxed spring 2022 can be an overcoil which provides second wire 2020 the ability to compress and move the framework in that direction. An artisan will understand that different combinations of compressed and relaxed springs can be utilized to steer the framework as desired.

The waveform shape of the components described herein can provide additional spring force if no spring is used in conjunction with a coupling device wire or additional spring force if a coupling device spring is used. This spring force can return the framework to plumb when a force is not being applied to one or more coupling members. In other words, the waveforms can provide "anti-steer."

The waveform shape of the components described herein can also provide bendability of the framework without collapse or crushing of the channels running though a framework unlike braided tubing.

Figure 22:
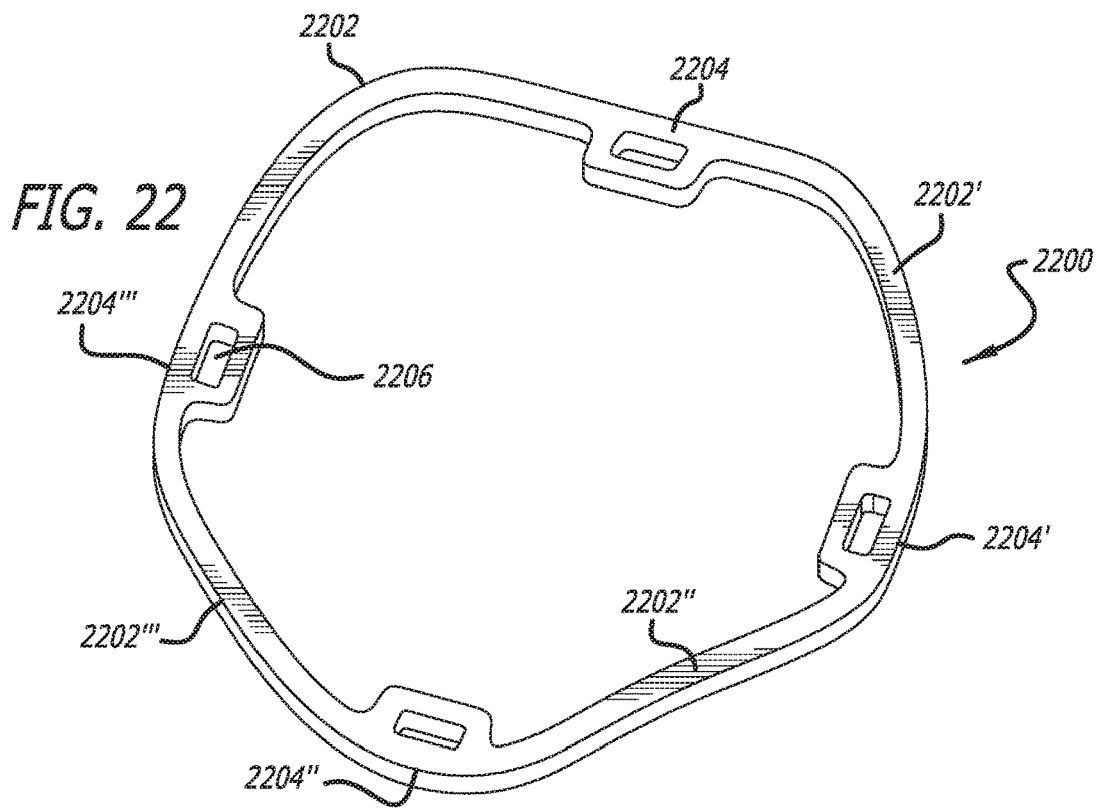
FIG. 22 illustrates another example structural component including rectangular holes.

Structural components can include holes with various shapes to create conduits through a device with a particular shape. For example, FIG. 22 illustrates a structural component 2200 including four peaks 2202, 2202', 2202'', 2202''' wherein each valley 2204, 2204', 2204'', 2204''' includes a rectangular hole 2206. As will be appreciated, any non-wave element used that can have complimentary shaped holes. Other hole shapes can include, circle, oval, ellipse, square, triangle, trapezoid, and the like.

The frameworks and structures described can further include a cover, jacket and or other coating to create individual lumens with patency, capable of passing fluids and gases as well as mechanical and electrical components. A coating or jacket can be translucent. In other embodiments, it can be opaque. A coating jacket may only cover the outside of a framework.

Figure 23:
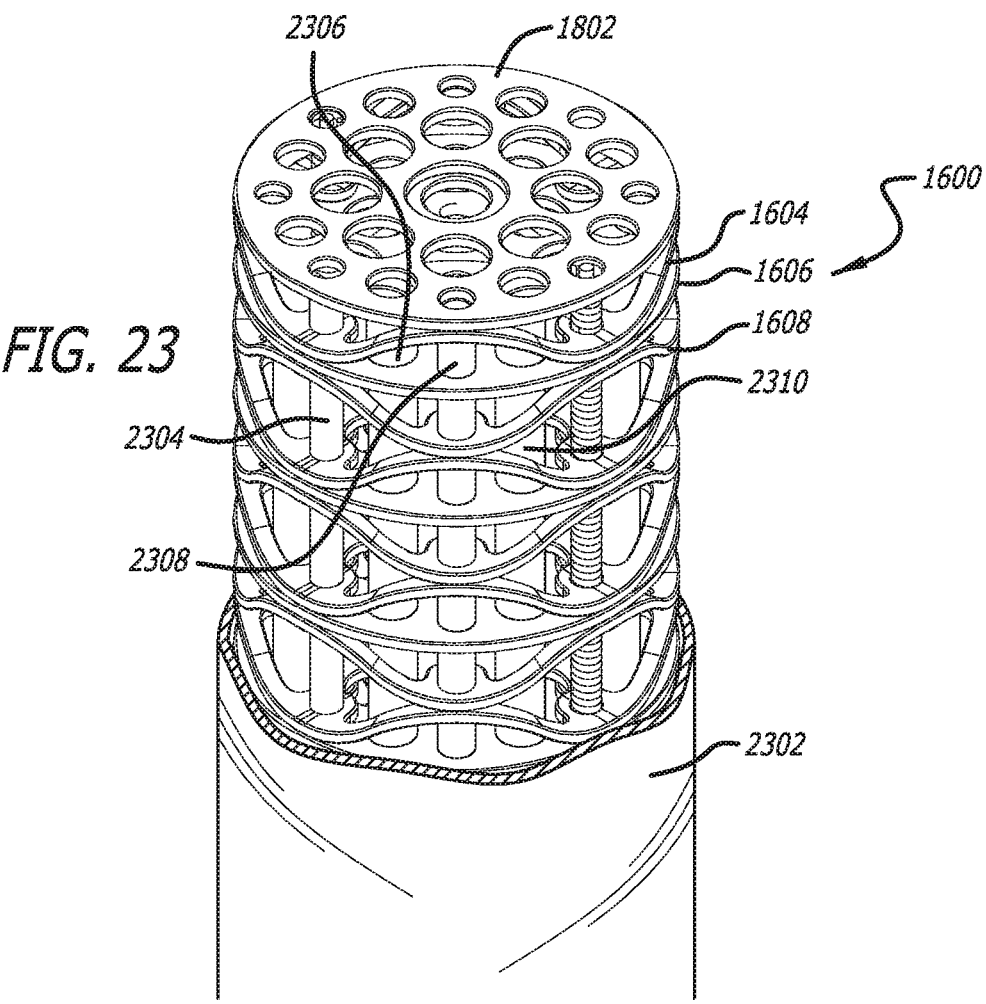
FIG. 23 illustrates the flexible framework of FIG. 20 including a jacket.

For example, as illustrated in FIG. 23, framework 1600 including a top plate or anchor plate 2002 can include a jacket 2302. Jacket can cover a portion of the framework, substantially all of the framework (e.g., leaving the ends uncovered), or completely covered. Further, although illustrated on framework 1600, jacket 2302 can be applied around any framework described herein. The material used to form a jacket can be reinforced tubing such as braided or coiled tubing. For example, braided polymer or stainless steel can be used for reinforcement.

Jackets and coatings can be formed of any suitable polymer. Polymers can include, but are not limited to, poly(L-lactic acid), polycaprolactone, poly(lactide-co-glycolide), poly(ethylene-vinyl acetate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly (ether-esters) (e.g., PEO/PLA), polyurethanes, silicones, polyesters, polyolefins, polyisobutylene and ethylene-alphaolefin copolymers, acrylic polymers and copolymers, ethylene-co-vinylacetate, polybutylmethacrylate, vinyl halide polymers and copolymers (e.g., polyvinyl chloride), polyvinyl ethers (e.g., polyvinyl methyl ether), polyvinylidene halides (e.g., polyvinylidene fluoride and polyvinylidene chloride), polyacrylonitrile, polyvinyl ketones, polyvinyl aromatics (e.g., polystyrene), polyvinyl esters (e.g., polyvinyl acetate), acrylonitrile-styrene copolymers, ABS resins, polyamides (e.g., Nylon 11, Nylon 12, Nylon 66 and polycaprolactam), polycarbonates, polyoxymethylenes, polyimides, PET, polyethers, polyurethanes, rayon, cellophane, carboxymethyl cellulose, and combinations thereof.

In some embodiments, jackets and coatings can be formed of polyether block amides, thermoplastic elastomers such as a rubber, polybutylene terephthalate, styrene elastomers, hytrel, polyester elastomers, or combinations thereof.

In one embodiment, a jacket or coating can be formed of a polyether block amide.

In one embodiment, a jacket or coating can be formed of a thermoplastic elastomer.

In one embodiment, a jacket or coating can be formed of a polybutylene terephthalate (PBT).

In one embodiment, a jacket or coating can be formed of a styrene elastomer.

In one embodiment, a jacket or coating can be formed of a HYTREL® polymer.

In one embodiment, a jacket or coating can be formed of a polyester elastomer.

In other embodiments, one or more tubes can be fed through the lumen of a framework to create multiple internal lumens capable of passing fluids and gases as well as mechanical and electrical components.

Framework 1600 in FIG. 23 also includes first conduit tube 2304, second conduit tube 2306, third conduit tube 2308, and forth conduit tube 2310. Any number of conduit tubes can be included in a frame work as space allows. For example, a framework can include two, three, four five, six, seven, eight, nine, ten, eleven, twelve, 13, 14, 15 or more conduit tubes within its perimeter. Each conduit tube can be configured to carry a different device or substance. Further, each conduit tube can be independently sized as needed. Although illustrated within framework 1600, conduit tubes can be applied within any framework described herein.

Conduit tubes can carry machinery, wires, fluids, electronics, and the like without kinking because of the protected lumen of the described frameworks. In some embodiments, conduit tubes need not travel the entire length of the flexible structure. For example, a conduit tube may terminate short of the end of the flexible structure. In such an embodiment, a conduit tube can house a pre-formed stylet(s) or wires that when projected out the end of the conduit can be used to steer or influence the shape of the structure through channels that extend farther through the flexible structure. In some embodiments, conduits can be formed in the center of a spring and that spring can house a stylet(s). In other embodiments, conduit tubes need not be tubes, but rather can be bare or insulated wire, fiber optics, polymeric filaments or the like.

In some embodiments, a conduit tube can be used to add rigidity to a flexible structure by increasing the structure's bending resistance. In some embodiments, a conduit tube can be placed at a particular length of the flexible structure or at a pattern of lengths to provide various bending resistances as different portions of the flexible structure.

In other embodiments, a conduit tube may not be a tube at all, but rather a solid filament of polymer or metal. The polymer, metal, or combination thereof can be selected for its bending resistance properties to provide desired rigidity and bending resistance to at least a portion of the flexible structure.

Figure 24:
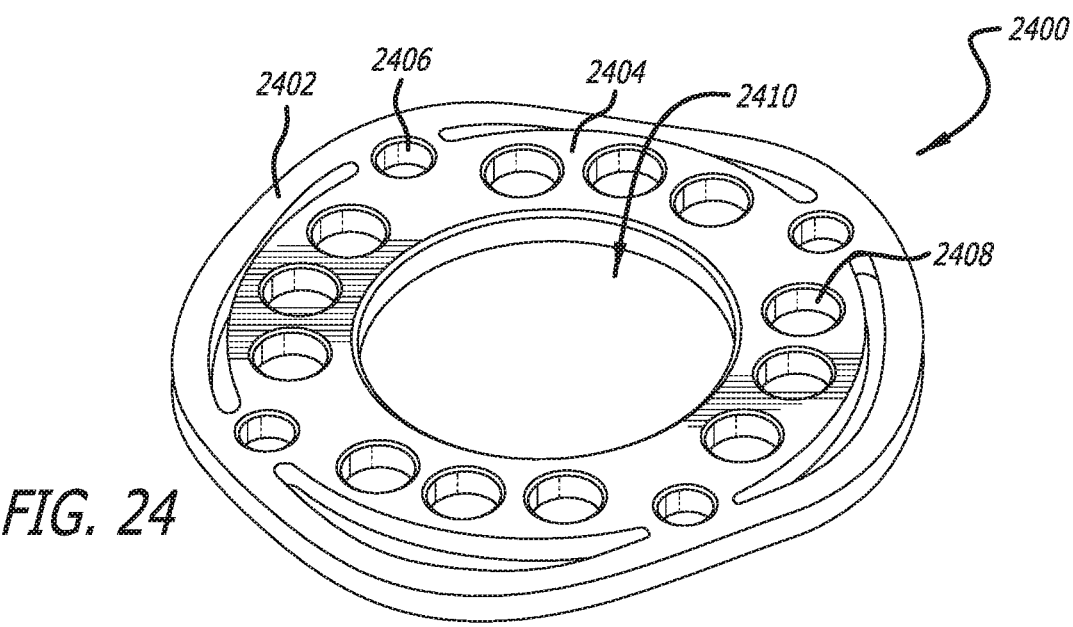
FIG. 24 illustrates an example structural element/non-wave element combination component.

The frameworks described herein can further include structural components that combine structural components and non-wave elements into one multiuse component. For example, FIG. 24 illustrates structural stabilizing component 2400. Structural stabilizing component 2400 includes the waveform portion 2402 of a structural component as described herein and also a non-wave element portion 2404 in its center to aid in stabilizing an internal lumen. Waveform portion 2402 can include at least one hole 2406. In one embodiment, waveform portion 2402 can include two, three, four five, six, seven, eight, nine, ten, eleven, twelve, thirteen, fourteen or fifteen or more holes 2406. Non-wave element portion 2404 can also include at least one hole 2408. In one embodiment, non-wave element portion 2404 can include two, three, four five, six, seven, eight, nine, ten, eleven, twelve, thirteen, fourteen or fifteen or more holes 2408. In one embodiment, waveform portion 2402 includes four holes 2406 and non-wave element portion 2404 includes 13 holes 2408. One of holes 2408 can be a larger center conduit hole 2410.

This multiuse component can be combined with other similar multiuse components to form a uniform framework or it can be incorporated with other structural components and non-wave elements to form various frameworks with different characteristics and mechanical properties. The design of this individual multiuse component can also be assembled into a flexible structure using the same methods and other components as other frameworks described herein.

Figure 25:
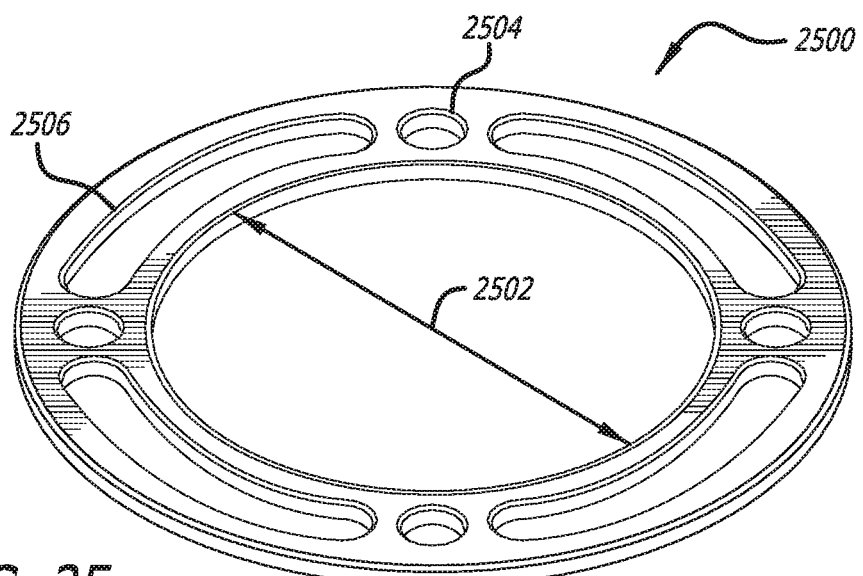
FIG. 25 illustrates an example non-wave element.

Non-wave elements can also have different configurations dependent on an application. For example, as illustrated in FIG. 25, open center non-wave element 2500 includes a large inner diameter 2502 that is substantially circular. Four holes 2504 are included that can be used to secure a framework or to feed a conduit line through each. Further, four radial voids 2506 are included for horizontal movement of conduit lines, wires, and the like. The number of holes and radial voids can vary depending on the design of the non-wave element. In some embodiments, non-wave element configurations may accommodate a high number of conductors and/or a ribbon wire conductor or stiffener(s). These configurations can include curved holes to match the radial shape which may prevent structural bending in any direction for a given length.

Figure 26:
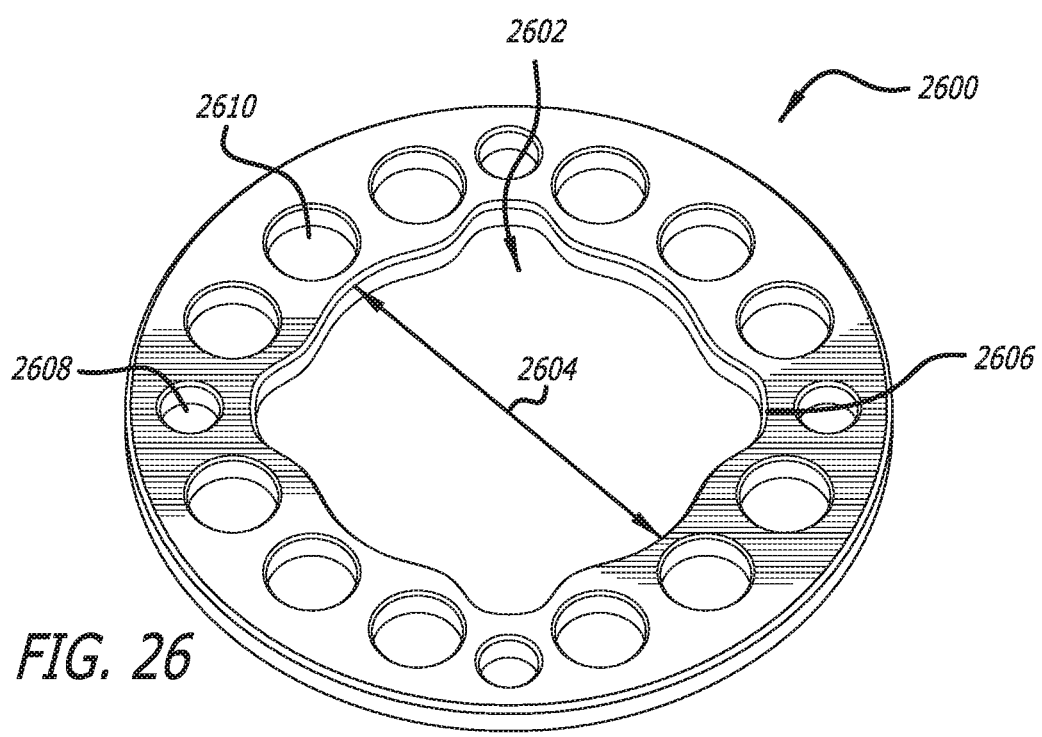
FIG. 26 illustrates another example non-wave element.

Another example non-wave element is illustrated in FIG. 26. Non-wave element 2600 includes a substantially square inner conduit hole 2602. Hole 2602 can have a edge length 2604. Hole 2602 can have curved features 2606 along its edges to facilitate placement of lumens there through. Four holes 2608 are included that can be used to secure a framework or to feed a conduit line there through. Further, 12 larger holes 2610 are included and can be used to feed additional conduit lines, wires, and the like. The number of holes, larger holes, and the size and shape of inner conduit hole can vary depending on the design of the non-wave element.

Figure 27:
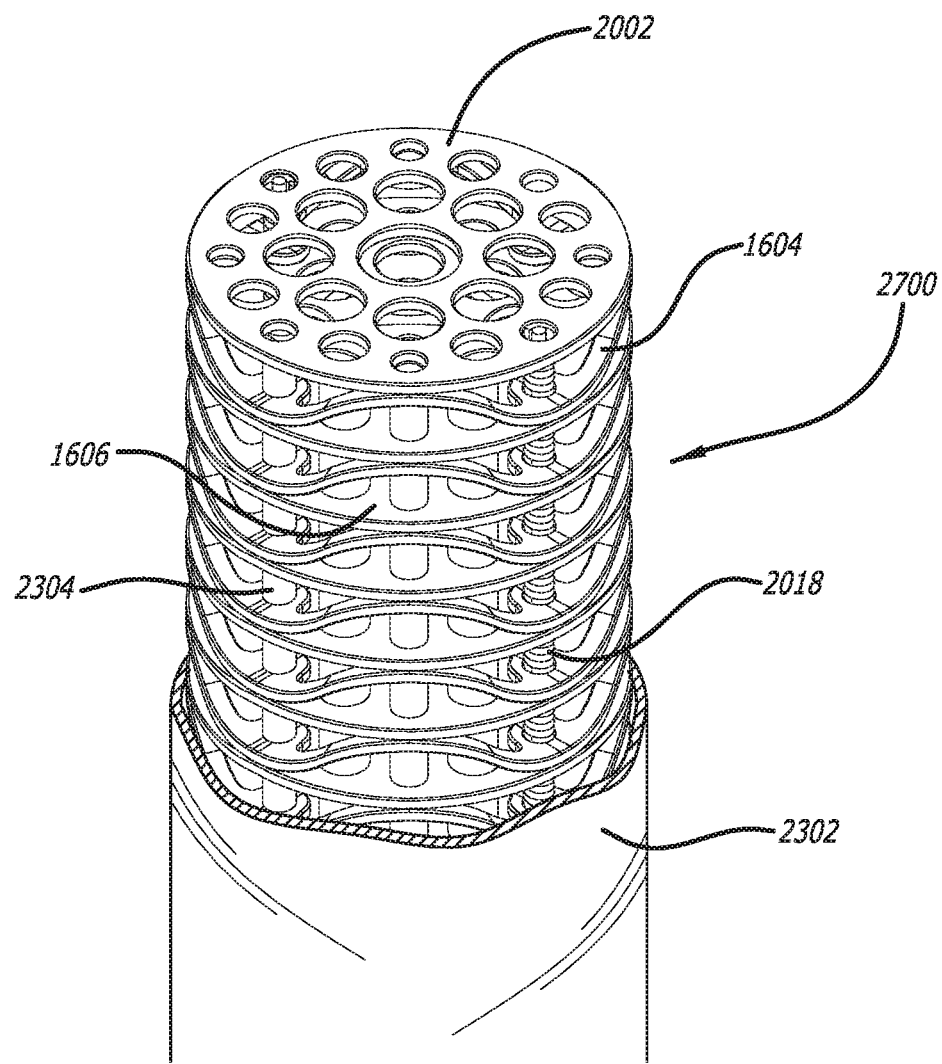
FIG. 27 illustrates another example flexible framework including a jacket.

Another example structure is illustrated in FIG. 27. Framework 2700 includes anchor plate 2002 attached to the top of the framework. The framework then includes repeat units of first component 1604 and spacer ring 1606. Here, only one wave component is used between spacer rings and the wave components are all parallel to each other.

This configuration of framework 2700 can provide enhanced characteristics to the structure. The enhancement can be that the non-wave elements are closer together based on wave height resulting in a smaller gap between the non-wave elements. This creates gap reduction can create a more continuous lumen for feeding devices, wires, or the like during use. This configuration can also change the flexibility in bending and transmission of torque of the structure because of the gap reduction. In some embodiments, the flexible structure can be more rigid and/or present a larger bending resistance because of the reduction in wave height and gap distance.

In other embodiments, a flexible structure can be made more flexible and or present a smaller bending resistance if more wave elements are included between non-wave elements. In some embodiments, the flexible structure can be less rigid and/or present a smaller bending resistance because of the increase in wave height and gap distance.

Structural components, non-wave elements, combination structural components/non-wave elements, and top plates can be formed using any appropriate technique. Techniques can include CNC machining, photo/chemical machining, laser cutting, plasma cutting, lathing, casting, injection molding, milling, or additive manufacturing processes such as 3D printing or the like. A combination of the above techniques can also be used.

In one embodiment, the components can be punched from sheets of metal or polymer whereby several, for example several hundred or several thousand can be punched in a single/continuous sheet of metal or polymer. A press or a die can be used to form the wave shape of the wave elements. In one embodiment, the wave elements can be formed by the punch wherein the punch includes a die or press surface.

In other embodiments, the components can be formed using photochemical machining/etching techniques. Once etched, the wave components can be formed by a die or press.

If structure components are formed of polymer, they can be formed using an injection molding process. There, pre-formed casts are filled with polymer and allowed to cool and form.

Whether metal or polymer, structural components can be formed as connected structures directly. For example, flexible structures can be initially created as a linear chain of components that is photochemical machined/etch/stamped to include appropriate waveform and non-waveforms and then folded in an accordion manner in order to form the flexible structure. Once properly folded, further soldering, bonding, gluing, brazing or the like may be required to finalize a flexible structure. Also, once assembled, any springs, conduits or the like can be added to the structure. In some embodiments, however, springs and/or conduits need to be added as the structure is being assembled.

There herein described flexible structures can include wires that move the structures that are connected to motors/actuators to actuate the structures. The motors can be manually controlled or computer controlled. A computer controlled motor can be used, for example, in a robotic system.

In other embodiments, the wires can be connected to manually moveable connection points such as those at the end of a catheter that allow a user to manually move the flexible structure.

Any combination of structural component and/or non-wave elements described herein can be used to form a flexible framework.

Example 1

A Medical Device

One industry where a described framework can be applicable is the medical device industry where flexible structures are commonly required. Examples where frameworks can be applicable include, but are not limited to, joints for prosthetic devices, devices such as catheters to facilitate access to various anatomies, or other therapeutic or non-therapeutic devices that require mechanical articulation but maintain the mechanical or material properties required for the design. Particular to the area of catheter design is that of steerable/articulatable structures which maintain the cross sectional shape, inner diameter and outer diameter, when steered. Such catheters are required to have mechanical properties such as hoop strength to prevent collapsing or crushing of the lumen, torsional stiffness required for transfer of torque for rotating and manipulation of the catheter and column strength for pushing or pulling the catheter either inside another catheter or in a vein or artery or other anatomies. The inner diameter of a catheter can be designed to allow other catheters or therapeutic mechanical/electro-mechanical devices to be fed through the inside diameter or directly integrated into the structure.

Example 2

A Lure

Frameworks as described herein can be useful as a fishing lure component. Various cross sectional shapes can be used, such as elliptical, to resemble fish bait or such as round, to resemble worms. The inside design of various configurations can be important because through ports or holes may be needed to accommodate tensile or compression members in the structure to prevent failure.

A series of wire and compression springs can be fed through internal lumens and attached or bonded to a top plate. A motor(s) can be attached to the opposite end of the wires. The motor(s) can pull and push the wire, thereby moving/steering the framework. The movement can be random or preprogrammed and stored in memory and performed by a microprocessor.

The swimming action of a lure can be duplicated by using material of greater thickness or shorter joint spacing on the posterior section and thinner material or longer joint spacing on the anterior section.

A jacket can be placed over the framework. The jacket can be painted and/or molded to resemble a fish, worm, or other bait item. In some embodiments, when used as a luer, elements can be joined with no wave form elements but alternatively joined for flexibility which creates a continuous surface which can be painted or decorated like a fish or plated silver or gold. In some embodiments, when used as a luer, a structure may not need a jacket.

Example 3

A Camera

Frameworks as described herein can be useful as an articulable camera system. Various cross sectional shapes can be used, such as spherical, that allow the camera system to be navigated trough a particular substance, area, or lumen. The center lumen of the framework can be used to carry power and data connections to and from the camera for real-time video. Other lumens can be used for fiber optic lighting for image enhancement for the camera.

The camera system's flexible structure can be coated or otherwise covered with a rubber layer to prevent liquids from interacting with the power and/or data lines running through the flexible structure.

A camera(s) can be attached and sealed onto the front end of the flexible structure and attached to the power and/or data lines. Wires and compression springs as described herein can be run through conduits in the flexible structure in order to steer the camera system.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

I claim:

1. A flexible framework for a medical device including:
   a plurality of structural components including:
   a first flexible annular structural component having an axial height measured from a top surface to a bottom surface that is constant around a perimeter of the first flexible annular structural component, wherein the axial height is less than or equal to a radial thickness measured from an outer perimeter to an inner perimeter, wherein the first flexible annular structural component includes a waveform including a first apex, and wherein the perimeter includes at least one bulge that includes a first conduit hole;
   a second flexible annular structural component having an axial height measured from a top surface to a bottom surface that is constant around a perimeter of the second flexible annular structural component, wherein the axial height is less than or equal to a radial thickness measured from an outer perimeter to an inner perimeter, wherein the second flexible annular structural component includes a waveform including a second apex, and wherein the perimeter includes at least one bulge that includes a second conduit hole; and
   a rigid structural component having an axial height measured from a top surface to a bottom surface that is constant around a perimeter of the rigid structural component, and wherein the rigid structural component includes a third conduit hole;
   wherein the first flexible annular structural component, the second flexible annular structural component, and the rigid structural component are stacked such that the first conduit hole, the second conduit hole, and the third conduit hole align,
   wherein the plurality of structural components is configured to form at least one internal conduit, and
   wherein the first apex is joined to the second apex by an adhesive, a solder, a weld, a braze, a plating, or a diffusion bonding.

2. The flexible framework of claim 1, further including a coating.

3. The flexible framework of claim 1, further including a jacket.

4. The flexible framework of claim 1, wherein the rigid structural component includes at least one internal conduit hole in addition to the third conduit hole.

5. The flexible framework of claim 1, wherein the first flexible annular structural component, the second flexible annular structural component, or both are bonded to the rigid structural component.

6. The flexible framework of claim 1, further including at least one wire and compression spring combination configured to traverse at least one of the at least one internal conduits.

7. The flexible framework of claim 6 comprising two wire and compression spring combinations.

8. The flexible framework of claim 1, further including at least one conduit tube traversing at least one of the at least one internal conduits.

9. The flexible framework of claim 1, wherein the waveform includes at least one complete wave.

10. The flexible framework of claim 1, wherein the waveform includes two complete waves.

11. The flexible framework of claim 1, wherein the waveform includes three complete waves.

12. The flexible framework of claim 1, wherein the waveform includes four complete waves.

13. The flexible framework of claim 1, further including a top plate.

* * * * *